US012637656B2

(12) United States Patent
Fojcik et al.

(10) Patent No.: US 12,637,656 B2
(45) Date of Patent: May 26, 2026

(54) RECOMBINANT YEAST CAPABLE OF PRODUCING CAFFEIC ACID AND/OR FERULIC ACID

(71) Applicant: ABOLIS BIOTECHNOLOGIES, Evry (FR)

(72) Inventors: Clémentine Fojcik, Palaiseau (FR); André Le Jeune, Draveil (FR); Lorène Telot, Courcouronnes (FR); Cyril Saguez, Champlan (FR)

(73) Assignee: ABOLIS BIOTECHNOLOGIES, Evry (FR)

( * ) Notice: Subject to any disclaimer, the term of this patent is extended or adjusted under 35 U.S.C. 154(b) by 834 days.

(21) Appl. No.: 17/774,374

(22) PCT Filed: Nov. 6, 2020

(86) PCT No.: PCT/FR2020/052021
§ 371 (c)(1),
(2) Date: May 4, 2022

(87) PCT Pub. No.: WO2021/089961
PCT Pub. Date: May 14, 2021

(65) Prior Publication Data

US 2022/0372431 A1 Nov. 24, 2022

(30) Foreign Application Priority Data

Nov. 8, 2019 (FR) ...................................... 1912573

(51) Int. Cl.
*C12N 1/16* (2026.01)
*C12N 9/16* (2006.01)
*C12N 15/52* (2006.01)

(52) U.S. Cl.
CPC ................. *C12N 1/16* (2013.01); *C12N 9/16* (2013.01); *C12N 15/52* (2013.01); *C12Y 301/01042* (2013.01)

(58) Field of Classification Search
CPC . C12N 1/16; C12N 9/16; C12N 15/32; C12Y 301/01042
See application file for complete search history.

(56) References Cited

PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
International Search Report and Written Opinion in corresponding International Patent Application No. PCT/FR2020/052021 dated May 14, 2021. (English translation attached.).
Annabel Nieter et al, "Heterologous production and characterization of a chlorogenic acid esterase from Ustilago maydis with a potential use in baking", Food Chemistry, vol. 209, Oct. 1, 2016, p. 1-9.
Nieter Annabel et al, "Ap-coumaroyl esterase from Rhizoctonia solani with a pronounced chlorogenic acid esterase activity", New Biotechnology, Elsevier BV, NL,vol. 37, Jan. 31, 2017 (Jan. 31, 2017), p. 153-161.
Lanqing Liu et al., "Engineering the Biosynthesis of Caffeic Acid in *Saccharomyces cerevisiae* with Heterologous Enzyme Combinations", Engineering, vol. 5, No. 2, Apr. 1, 2019 (Apr. 1, 2019), p. 287-295.
João Rainha et al, "Synthetic Biology Approaches to Engineer *Saccharomyces cerevisiae* towards the Industrial Production of Valuable Polyphenolic Compounds", Life,vol. 10, No. 5, May 5, 2020 (May 2, 2020), p. 56.
Ruibing Chen et al, "Advanced Strategies for Production of Natural Products in Yeast", DOI: 10.1016 jisci.2020.100879 external link, Mar. 27, 2020 (Mar. 27, 2020), p. 100879.
Damla Huccetogullari et al, "Metabolic engineering of microorganisms for production of aromatic compounds", Microbial Cell Factories,vol. 18, No. 1, Feb. 1, 2019 (Feb. 1, 2019).

* cited by examiner

*Primary Examiner* — Robert A Zeman
(74) *Attorney, Agent, or Firm* — Leason Ellis LLP

(57) ABSTRACT

The present invention relates to a recombinant microorganism, preferably a recombinant yeast, capable of producing caffeic acid comprising a heterologous gene coding for an enzyme of the hydrolase family capable of breaking, preferably of hydrolyzing, the caffeoyl-shikimate bond to produce caffeic acid from caffeoyl-shikimate. Said microorganism, preferably said recombinant yeast, may also be capable of producing ferulic acid from the caffeic acid obtained. The present invention also relates to a method for producing caffeic acid and a method for producing caffeic acid and/or ferulic acid, using microorganisms, preferably yeasts, according to the invention. Finally, the invention also relates to the use of microorganisms, preferably yeasts, according to the invention to produce caffeic acid and/or ferulic acid.

4 Claims, 7 Drawing Sheets

Specification includes a Sequence Listing.

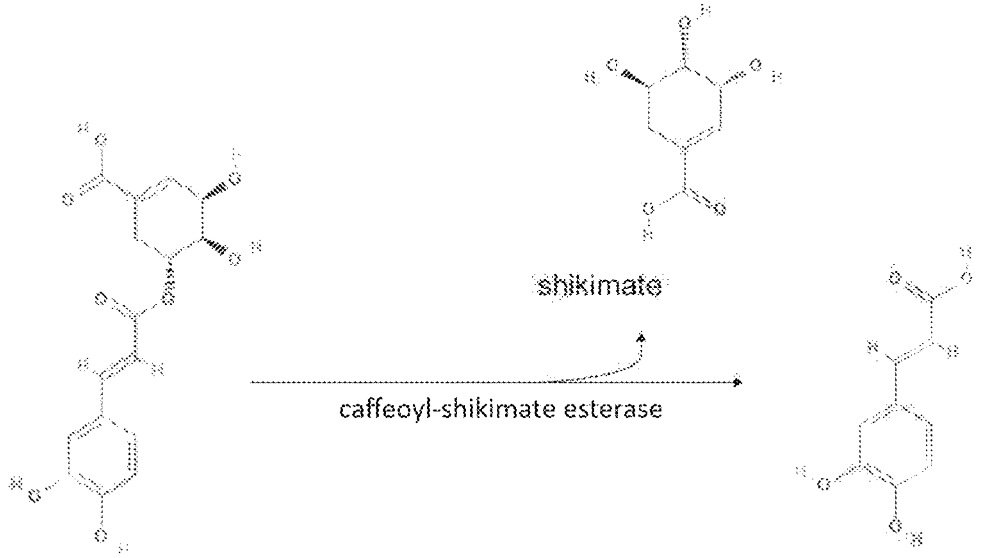

Fig. 1 shikimate caffeoyl-shikimate esterase caffeoyl-shikimate caffeic acid

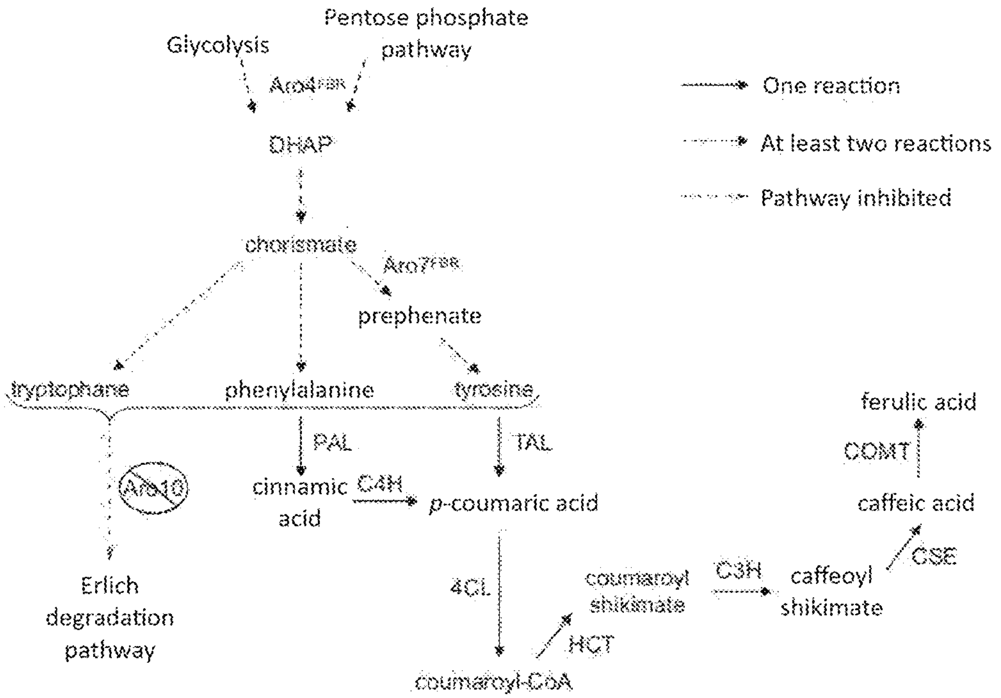

Fig. 2

Glycolysis    Pentose phosphate
                    pathway

Aro4$^{FBR}$

DHAP chorismate

Aro7$^{FBR}$ prephenate tryptophane    phenylalanine    tyrosine ferulic acid

COMT caffeic acid

Aro10

PAL

TAL cinnamic    C4H
acid        p-coumaric acid

CSE

Erlich
degradation
pathway

4CL coumaroyl
shikimate    C3H    caffeoyl
                    shikimate

HCT coumaroyl-CoA

———▶ One reaction

----▶ At least two reactions

·-·-·▶ Pathway inhibited

SEQUENCE LISTING

<160> NUMBER OF SEQ ID NOS: 15

<210> SEQ ID NO 1
<211> LENGTH: 561
<212> TYPE: PRT
<213> ORGANISM: Arabidopsis thaliana
<220> FEATURE:
<223> OTHER INFORMATION: 4CL

<400> SEQUENCE: 1

Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
    130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Asp Val Val Ala Leu Pro
        195                 200                 205

Tyr Ser Ser Gly Thr Thr Gly Leu Pro Lys Gly Val Met Leu Thr His
    210                 215                 220

Lys Gly Leu Val Thr Ser Val Ala Gln Gln Val Asp Gly Glu Asn Pro
225                 230                 235                 240

Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
    290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
                325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly

-continued

```
        355                 360                 365

Phe Ala Lys Glu Pro Phe Pro Val Lys Ser Gly Ala Cys Gly Thr Val
    370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
                405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
    450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
    530                 535                 540

Ser Gly Lys Ile Leu Arg Lys Asp Leu Arg Ala Lys Leu Ala Asn Gly
545                 550                 555                 560

Leu


<210> SEQ ID NO 2
<211> LENGTH: 363
<212> TYPE: PRT
<213> ORGANISM: Arabidopsis thaliana
<220> FEATURE:
<223> OTHER INFORMATION: COMT

<400> SEQUENCE: 2

Met Gly Ser Thr Ala Glu Thr Gln Leu Thr Pro Val Gln Val Thr Asp
1               5                   10                  15

Asp Glu Ala Ala Leu Phe Ala Met Gln Leu Ala Ser Ala Ser Val Leu
            20                  25                  30

Pro Met Ala Leu Lys Ser Ala Leu Glu Leu Asp Leu Leu Glu Ile Met
        35                  40                  45

Ala Lys Asn Gly Ser Pro Met Ser Pro Thr Glu Ile Ala Ser Lys Leu
    50                  55                  60

Pro Thr Lys Asn Pro Glu Ala Pro Val Met Leu Asp Arg Ile Leu Arg
65                  70                  75                  80

Leu Leu Thr Ser Tyr Ser Val Leu Thr Cys Ser Asn Arg Lys Leu Ser
                85                  90                  95

Gly Asp Gly Val Glu Arg Ile Tyr Gly Leu Gly Pro Val Cys Lys Tyr
            100                 105                 110

Leu Thr Lys Asn Glu Asp Gly Val Ser Ile Ala Ala Leu Cys Leu Met
        115                 120                 125

Asn Gln Asp Lys Val Leu Met Glu Ser Trp Tyr His Leu Lys Asp Ala
    130                 135                 140

Ile Leu Asp Gly Gly Ile Pro Phe Asn Lys Ala Tyr Gly Met Ser Ala
145                 150                 155                 160
```

```
Phe Glu Tyr His Gly Thr Asp Pro Arg Phe Asn Lys Val Phe Asn Asn
                165                 170                 175

Gly Met Ser Asn His Ser Thr Ile Thr Met Lys Lys Ile Leu Glu Thr
            180                 185                 190

Tyr Lys Gly Phe Glu Gly Leu Thr Ser Leu Val Asp Val Gly Gly Gly
        195                 200                 205

Ile Gly Ala Thr Leu Lys Met Ile Val Ser Lys Tyr Pro Asn Leu Lys
    210                 215                 220

Gly Ile Asn Phe Asp Leu Pro His Val Ile Glu Asp Ala Pro Ser His
225                 230                 235                 240

Pro Gly Ile Glu His Val Gly Gly Asp Met Phe Val Ser Val Pro Lys
                245                 250                 255

Gly Asp Ala Ile Phe Met Lys Trp Ile Cys His Asp Trp Ser Asp Glu
            260                 265                 270

His Cys Val Lys Phe Leu Lys Asn Cys Tyr Glu Ser Leu Pro Glu Asp
        275                 280                 285

Gly Lys Val Ile Leu Ala Glu Cys Ile Leu Pro Glu Thr Pro Asp Ser
    290                 295                 300

Ser Leu Ser Thr Lys Gln Val Val His Val Asp Cys Ile Met Leu Ala
305                 310                 315                 320

His Asn Pro Gly Gly Lys Glu Arg Thr Glu Lys Glu Phe Glu Ala Leu
                325                 330                 335

Ala Lys Ala Ser Gly Phe Lys Gly Ile Lys Val Val Cys Asp Ala Phe
            340                 345                 350

Gly Val Asn Leu Ile Glu Leu Leu Lys Lys Leu
        355                 360


<210> SEQ ID NO 3
<211> LENGTH: 332
<212> TYPE: PRT
<213> ORGANISM: Arabidopsis thaliana
<220> FEATURE:
<223> OTHER INFORMATION: CSE

<400> SEQUENCE: 3

Met Pro Ser Glu Ala Glu Ser Ser Ala Asn Ser Ala Pro Ala Thr Pro
1               5                   10                  15

Pro Pro Pro Pro Asn Phe Trp Gly Thr Met Pro Glu Glu Glu Tyr Tyr
            20                  25                  30

Thr Ser Gln Gly Val Arg Asn Ser Lys Ser Tyr Phe Glu Thr Pro Asn
        35                  40                  45

Gly Lys Leu Phe Thr Gln Ser Phe Leu Pro Leu Asp Gly Glu Ile Lys
    50                  55                  60

Gly Thr Val Tyr Met Ser His Gly Tyr Gly Ser Asp Thr Ser Trp Met
65                  70                  75                  80

Phe Gln Lys Ile Cys Met Ser Phe Ser Ser Trp Gly Tyr Ala Val Phe
                85                  90                  95

Ala Ala Asp Leu Leu Gly His Gly Arg Ser Asp Gly Ile Arg Cys Tyr
            100                 105                 110

Met Gly Asp Met Glu Lys Val Ala Ala Thr Ser Leu Ala Phe Phe Lys
        115                 120                 125

His Val Arg Cys Ser Asp Pro Tyr Lys Asp Leu Pro Ala Phe Leu Phe
    130                 135                 140

Gly Glu Ser Met Gly Gly Leu Val Thr Leu Leu Met Tyr Phe Gln Ser
145                 150                 155                 160
```

```
Glu Pro Glu Thr Trp Thr Gly Leu Met Phe Ser Ala Pro Leu Phe Val
                165                 170                 175

Ile Pro Glu Asp Met Lys Pro Ser Lys Ala His Leu Phe Ala Tyr Gly
            180                 185                 190

Leu Leu Phe Gly Leu Ala Asp Thr Trp Ala Ala Met Pro Asp Asn Lys
        195                 200                 205

Met Val Gly Lys Ala Ile Lys Asp Pro Glu Lys Leu Lys Ile Ile Ala
    210                 215                 220

Ser Asn Pro Gln Arg Tyr Thr Gly Lys Pro Arg Val Gly Thr Met Arg
225                 230                 235                 240

Glu Leu Leu Arg Lys Thr Gln Tyr Val Gln Glu Asn Phe Gly Lys Val
                245                 250                 255

Thr Ile Pro Val Phe Thr Ala His Gly Thr Ala Asp Gly Val Thr Cys
            260                 265                 270

Pro Thr Ser Ser Lys Leu Leu Tyr Glu Lys Ala Ser Ser Ala Asp Lys
        275                 280                 285

Thr Leu Lys Ile Tyr Glu Gly Met Tyr His Ser Leu Ile Gln Gly Glu
    290                 295                 300

Pro Asp Glu Asn Ala Glu Ile Val Leu Lys Asp Met Arg Glu Trp Ile
305                 310                 315                 320

Asp Glu Lys Val Lys Lys Tyr Gly Ser Lys Thr Ala
                325                 330


<210> SEQ ID NO 4
<211> LENGTH: 262
<212> TYPE: PRT
<213> ORGANISM: Bifidobacterium animalis subsp. lactis
<220> FEATURE:
<223> OTHER INFORMATION: BiChlE

<400> SEQUENCE: 4

Met Thr Thr Ser Thr His Thr Glu Glu Ile Thr Val Met Arg Asp Gly
1               5                   10                  15

Leu Arg Leu His Gly Arg Ile Asp Ala Pro Gln Gly Glu Pro Lys Gly
            20                  25                  30

Pro Val Val Ile Leu Met His Gly Phe Met Ala Asp Leu Gly Tyr Glu
        35                  40                  45

Pro Gly Ser Leu Leu Gln Gln Val Ser Asp Gln Leu Val Glu Ala Gly
    50                  55                  60

Phe Thr Ser Val Arg Phe Asp Phe Asn Gly Arg Gly Asn Ser Asp Gly
65                  70                  75                  80

Ser Phe Ala Asn Ser Asp Val Cys Asn Gln Val Glu Asp Ala Ile Ala
                85                  90                  95

Val Leu Asn Phe Val Arg Asp Arg Phe Glu Pro Ala Glu Ile Ser Leu
            100                 105                 110

Leu Gly His Ser Gln Gly Gly Val Ile Ala Gly Met Thr Ala Gly Met
        115                 120                 125

Tyr Ala Asp Val Val His Ser Leu Val Leu Leu Ser Pro Ala Ala Ser
    130                 135                 140

Ile Lys Asp Asp Ala Leu Arg Gly Arg Val Leu Gly Val Pro Phe Asp
145                 150                 155                 160

Pro Tyr His Ile Pro Arg Arg Ile Ala Leu Ala Asp Gly Lys His Glu
                165                 170                 175

Val Ala Gly Lys Tyr Ser Arg Ile Ala Lys Thr Ile Pro Val Tyr Glu
            180                 185                 190
```

```
Ala Ala Ala Met Phe Lys Gly Pro Ala Leu Ala Ile Gln Gly Glu Gln
        195                 200                 205

Asp Lys Val Ile Asp Pro Ser Cys Ala His Asn Tyr Gly Asn Ala Met
    210                 215                 220

Ala Asn Cys Thr Val Ser Leu Tyr Thr Asn Leu Asp His Lys Phe Asn
225                 230                 235                 240

Gly Asp Asp Arg Met Arg Ala Ile Gly Glu Ala Val Ala Phe Leu Gln
                245                 250                 255

Thr His His Glu Val Ala
            260


<210> SEQ ID NO 5
<211> LENGTH: 508
<212> TYPE: PRT
<213> ORGANISM: Arabidopsis thaliana
<220> FEATURE:
<223> OTHER INFORMATION: C3H

<400> SEQUENCE: 5

Met Ser Trp Phe Leu Ile Ala Val Ala Thr Ile Ala Ala Val Val Ser
1               5                   10                  15

Tyr Lys Leu Ile Gln Arg Leu Arg Tyr Lys Phe Pro Pro Gly Pro Ser
            20                  25                  30

Pro Lys Pro Ile Val Gly Asn Leu Tyr Asp Ile Lys Pro Val Arg Phe
        35                  40                  45

Arg Cys Tyr Tyr Glu Trp Ala Gln Ser Tyr Gly Pro Ile Ile Ser Val
    50                  55                  60

Trp Ile Gly Ser Ile Leu Asn Val Val Val Ser Ser Ala Glu Leu Ala
65                  70                  75                  80

Lys Glu Val Leu Lys Glu His Asp Gln Lys Leu Ala Asp Arg His Arg
                85                  90                  95

Asn Arg Ser Thr Glu Ala Phe Ser Arg Asn Gly Gln Asp Leu Ile Trp
            100                 105                 110

Ala Asp Tyr Gly Pro His Tyr Val Lys Val Arg Lys Val Cys Thr Leu
        115                 120                 125

Glu Leu Phe Thr Pro Lys Arg Leu Glu Ser Leu Arg Pro Ile Arg Glu
    130                 135                 140

Asp Glu Val Thr Ala Met Val Glu Ser Val Phe Arg Asp Cys Asn Leu
145                 150                 155                 160

Pro Glu Asn Arg Ala Lys Gly Leu Gln Leu Arg Lys Tyr Leu Gly Ala
                165                 170                 175

Val Ala Phe Asn Asn Ile Thr Arg Leu Ala Phe Gly Lys Arg Phe Met
            180                 185                 190

Asn Ala Glu Gly Val Val Asp Glu Gln Gly Leu Glu Phe Lys Ala Ile
        195                 200                 205

Val Ser Asn Gly Leu Lys Leu Gly Ala Ser Leu Ser Ile Ala Glu His
    210                 215                 220

Ile Pro Trp Leu Arg Trp Met Phe Pro Ala Asp Glu Lys Ala Phe Ala
225                 230                 235                 240

Glu His Gly Ala Arg Arg Asp Arg Leu Thr Arg Ala Ile Met Glu Glu
                245                 250                 255

His Thr Leu Ala Arg Gln Lys Ser Ser Gly Ala Lys Gln His Phe Val
            260                 265                 270

Asp Ala Leu Leu Thr Leu Lys Asp Gln Tyr Asp Leu Ser Glu Asp Thr
        275                 280                 285
```

```
Ile Ile Gly Leu Leu Trp Asp Met Ile Thr Ala Gly Met Asp Thr Thr
    290                 295                 300

Ala Ile Thr Ala Glu Trp Ala Met Ala Glu Met Ile Lys Asn Pro Arg
305                 310                 315                 320

Val Gln Gln Lys Val Gln Glu Glu Phe Asp Arg Val Val Gly Leu Asp
                325                 330                 335

Arg Ile Leu Thr Glu Ala Asp Phe Ser Arg Leu Pro Tyr Leu Gln Cys
            340                 345                 350

Val Val Lys Glu Ser Phe Arg Leu His Pro Pro Thr Pro Leu Met Leu
        355                 360                 365

Pro His Arg Ser Asn Ala Asp Val Lys Ile Gly Gly Tyr Asp Ile Pro
    370                 375                 380

Lys Gly Ser Asn Val His Val Asn Val Trp Ala Val Ala Arg Asp Pro
385                 390                 395                 400

Ala Val Trp Lys Asn Pro Phe Glu Phe Arg Pro Glu Arg Phe Leu Glu
                405                 410                 415

Glu Asp Val Asp Met Lys Gly His Asp Phe Arg Leu Leu Pro Phe Gly
            420                 425                 430

Ala Gly Arg Arg Val Cys Pro Gly Ala Gln Leu Gly Ile Asn Leu Val
        435                 440                 445

Thr Ser Met Met Ser His Leu Leu His His Phe Val Trp Thr Pro Pro
    450                 455                 460

Gln Gly Thr Lys Pro Glu Glu Ile Asp Met Ser Glu Asn Pro Gly Leu
465                 470                 475                 480

Val Thr Tyr Met Arg Thr Pro Val Gln Ala Val Ala Thr Pro Arg Leu
                485                 490                 495

Pro Ser Asp Leu Tyr Lys Arg Val Pro Tyr Asp Met
            500                 505
```

<210> SEQ ID NO 6
<211> LENGTH: 714
<212> TYPE: PRT
<213> ORGANISM: Catharanthus roseus
<220> FEATURE:
<223> OTHER INFORMATION: CPR1

<400> SEQUENCE: 6

```
Met Asp Ser Ser Ser Glu Lys Leu Ser Pro Phe Glu Leu Met Ser Ala
1               5                   10                  15

Ile Leu Lys Gly Ala Lys Leu Asp Gly Ser Asn Ser Ser Asp Ser Gly
            20                  25                  30

Val Ala Val Ser Pro Ala Val Met Ala Met Leu Leu Glu Asn Lys Glu
        35                  40                  45

Leu Val Met Ile Leu Thr Thr Ser Val Ala Val Leu Ile Gly Cys Val
    50                  55                  60

Val Val Leu Ile Trp Arg Arg Ser Ser Gly Ser Gly Lys Lys Val Val
65                  70                  75                  80

Glu Pro Pro Lys Leu Ile Val Pro Lys Ser Val Val Glu Pro Glu Glu
                85                  90                  95

Ile Asp Glu Gly Lys Lys Lys Phe Thr Ile Phe Phe Gly Thr Gln Thr
            100                 105                 110

Gly Thr Ala Glu Gly Phe Ala Lys Ala Leu Ala Glu Glu Ala Lys Ala
        115                 120                 125

Arg Tyr Glu Lys Ala Val Ile Lys Val Ile Asp Ile Asp Asp Tyr Ala
    130                 135                 140
```

-continued

```
Ala Asp Asp Glu Glu Tyr Glu Glu Lys Phe Arg Lys Glu Thr Leu Ala
145                 150                 155                 160

Phe Phe Ile Leu Ala Thr Tyr Gly Asp Gly Glu Pro Thr Asp Asn Ala
                165                 170                 175

Ala Arg Phe Tyr Lys Trp Phe Val Glu Gly Asn Asp Arg Gly Asp Trp
            180                 185                 190

Leu Lys Asn Leu Gln Tyr Gly Val Phe Gly Leu Gly Asn Arg Gln Tyr
        195                 200                 205

Glu His Phe Asn Lys Ile Ala Lys Val Val Asp Glu Lys Val Ala Glu
    210                 215                 220

Gln Gly Gly Lys Arg Ile Val Pro Leu Val Leu Gly Asp Asp Asp Gln
225                 230                 235                 240

Cys Ile Glu Asp Asp Phe Ala Ala Trp Arg Glu Asn Val Trp Pro Glu
                245                 250                 255

Leu Asp Asn Leu Leu Arg Asp Glu Asp Asp Thr Thr Val Ser Thr Thr
            260                 265                 270

Tyr Thr Ala Ala Ile Pro Glu Tyr Arg Val Val Phe Pro Asp Lys Ser
        275                 280                 285

Asp Ser Leu Ile Ser Glu Ala Asn Gly His Ala Asn Gly Tyr Ala Asn
    290                 295                 300

Gly Asn Thr Val Tyr Asp Ala Gln His Pro Cys Arg Ser Asn Val Ala
305                 310                 315                 320

Val Arg Lys Glu Leu His Thr Pro Ala Ser Asp Arg Ser Cys Thr His
                325                 330                 335

Leu Asp Phe Asp Ile Ala Gly Thr Gly Leu Ser Tyr Gly Thr Gly Asp
            340                 345                 350

His Val Gly Val Tyr Cys Asp Asn Leu Ser Glu Thr Val Glu Glu Ala
        355                 360                 365

Glu Arg Leu Leu Asn Leu Pro Pro Glu Thr Tyr Phe Ser Leu His Ala
    370                 375                 380

Asp Lys Glu Asp Gly Thr Pro Leu Ala Gly Ser Ser Leu Pro Pro Pro
385                 390                 395                 400

Phe Pro Pro Cys Thr Leu Arg Thr Ala Leu Thr Arg Tyr Ala Asp Leu
                405                 410                 415

Leu Asn Thr Pro Lys Lys Ser Ala Leu Leu Ala Leu Ala Ala Tyr Ala
            420                 425                 430

Ser Asp Pro Asn Glu Ala Asp Arg Leu Lys Tyr Leu Ala Ser Pro Ala
        435                 440                 445

Gly Lys Asp Glu Tyr Ala Gln Ser Leu Val Ala Asn Gln Arg Ser Leu
    450                 455                 460

Leu Glu Val Met Ala Glu Phe Pro Ser Ala Lys Pro Pro Leu Gly Val
465                 470                 475                 480

Phe Phe Ala Ala Ile Ala Pro Arg Leu Gln Pro Arg Phe Tyr Ser Ile
                485                 490                 495

Ser Ser Ser Pro Arg Met Ala Pro Ser Arg Ile His Val Thr Cys Ala
            500                 505                 510

Leu Val Tyr Glu Lys Thr Pro Gly Gly Arg Ile His Lys Gly Val Cys
        515                 520                 525

Ser Thr Trp Met Lys Asn Ala Ile Pro Leu Glu Glu Ser Arg Asp Cys
    530                 535                 540

Ser Trp Ala Pro Ile Phe Val Arg Gln Ser Asn Phe Lys Leu Pro Ala
545                 550                 555                 560
```

-continued

```
Asp Pro Lys Val Pro Val Ile Met Ile Gly Pro Gly Thr Gly Leu Ala
                565                 570                 575

Pro Phe Arg Gly Phe Leu Gln Glu Arg Leu Ala Leu Lys Glu Glu Gly
            580                 585                 590

Ala Glu Leu Gly Thr Ala Val Phe Phe Phe Gly Cys Arg Asn Arg Lys
        595                 600                 605

Met Asp Tyr Ile Tyr Glu Asp Glu Leu Asn His Phe Leu Glu Ile Gly
    610                 615                 620

Ala Leu Ser Glu Leu Leu Val Ala Phe Ser Arg Glu Gly Pro Thr Lys
625                 630                 635                 640

Gln Tyr Val Gln His Lys Met Ala Glu Lys Ala Ser Asp Ile Trp Arg
                645                 650                 655

Met Ile Ser Asp Gly Ala Tyr Val Tyr Val Cys Gly Asp Ala Lys Gly
            660                 665                 670

Met Ala Arg Asp Val His Arg Thr Leu His Thr Ile Ala Gln Glu Gln
        675                 680                 685

Gly Ser Met Asp Ser Thr Gln Ala Glu Gly Phe Val Lys Asn Leu Gln
    690                 695                 700

Met Thr Gly Arg Tyr Leu Arg Asp Val Trp
705                 710


<210> SEQ ID NO 7
<211> LENGTH: 433
<212> TYPE: PRT
<213> ORGANISM: Arabidopsis thaliana
<220> FEATURE:
<223> OTHER INFORMATION: HCT

<400> SEQUENCE: 7

Met Lys Ile Asn Ile Arg Asp Ser Thr Met Val Arg Pro Ala Thr Glu
1               5                   10                  15

Thr Pro Ile Thr Asn Leu Trp Asn Ser Asn Val Asp Leu Val Ile Pro
            20                  25                  30

Arg Phe His Thr Pro Ser Val Tyr Phe Tyr Arg Pro Thr Gly Ala Ser
        35                  40                  45

Asn Phe Phe Asp Pro Gln Val Met Lys Glu Ala Leu Ser Lys Ala Leu
    50                  55                  60

Val Pro Phe Tyr Pro Met Ala Gly Arg Leu Lys Arg Asp Asp Asp Gly
65                  70                  75                  80

Arg Ile Glu Ile Asp Cys Asn Gly Ala Gly Val Leu Phe Val Val Ala
                85                  90                  95

Asp Thr Pro Ser Val Ile Asp Asp Phe Gly Asp Phe Ala Pro Thr Leu
            100                 105                 110

Asn Leu Arg Gln Leu Ile Pro Glu Val Asp His Ser Ala Gly Ile His
        115                 120                 125

Ser Phe Pro Leu Leu Val Leu Gln Val Thr Phe Phe Lys Cys Gly Gly
    130                 135                 140

Ala Ser Leu Gly Val Gly Met Gln His His Ala Ala Asp Gly Phe Ser
145                 150                 155                 160

Gly Leu His Phe Ile Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Ala Phe His His Val Glu Tyr Gln Pro Ala Pro Ser
        195                 200                 205
```

-continued

```
Met Lys Ile Pro Leu Asp Pro Ser Lys Ser Gly Pro Glu Asn Thr Thr
    210                 215                 220

Val Ser Ile Phe Lys Leu Thr Arg Asp Gln Leu Val Ala Leu Lys Ala
225                 230                 235                 240

Lys Ser Lys Glu Asp Gly Asn Thr Val Ser Tyr Ser Ser Tyr Glu Met
                245                 250                 255

Leu Ala Gly His Val Trp Arg Ser Val Gly Lys Ala Arg Gly Leu Pro
            260                 265                 270

Asn Asp Gln Glu Thr Lys Leu Tyr Ile Ala Thr Asp Gly Arg Ser Arg
        275                 280                 285

Leu Arg Pro Gln Leu Pro Pro Gly Tyr Phe Gly Asn Val Ile Phe Thr
    290                 295                 300

Ala Thr Pro Leu Ala Val Ala Gly Asp Leu Leu Ser Lys Pro Thr Trp
305                 310                 315                 320

Tyr Ala Ala Gly Gln Ile His Asp Phe Leu Val Arg Met Asp Asp Asn
                325                 330                 335

Tyr Leu Arg Ser Ala Leu Asp Tyr Leu Glu Met Gln Pro Asp Leu Ser
            340                 345                 350

Ala Leu Val Arg Gly Ala His Thr Tyr Lys Cys Pro Asn Leu Gly Ile
        355                 360                 365

Thr Ser Trp Val Arg Leu Pro Ile Tyr Asp Ala Asp Phe Gly Trp Gly
    370                 375                 380

Arg Pro Ile Phe Met Gly Pro Gly Gly Ile Pro Tyr Glu Gly Leu Ser
385                 390                 395                 400

Phe Val Leu Pro Ser Pro Thr Asn Asp Gly Ser Leu Ser Val Ala Ile
                405                 410                 415

Ala Leu Gln Ser Glu His Met Lys Leu Phe Glu Lys Phe Leu Phe Glu
            420                 425                 430

Ile
```

<210> SEQ ID NO 8
<211> LENGTH: 248
<212> TYPE: PRT
<213> ORGANISM: Lactobacillus johnsonii
<220> FEATURE:
<223> OTHER INFORMATION: LaChlE

<400> SEQUENCE: 8

```
Met Glu Thr Thr Ile Lys Arg Asp Gly Leu Asn Leu His Gly Leu Leu
1               5                   10                  15

Glu Gly Thr Asp Lys Ile Glu Asn Asp Thr Ile Ala Ile Leu Met His
            20                  25                  30

Gly Phe Lys Gly Asp Leu Gly Tyr Asp Asp Ser Lys Ile Leu Tyr Ala
        35                  40                  45

Leu Ser His Tyr Leu Asn Asp Gln Gly Leu Pro Thr Ile Arg Phe Asp
    50                  55                  60

Phe Asp Gly Cys Gly Lys Ser Asp Gly Lys Phe Glu Asp Met Thr Val
65                  70                  75                  80

Tyr Ser Glu Ile Leu Asp Gly Ile Lys Ile Leu Asp Tyr Val Arg Asn
                85                  90                  95

Thr Val Lys Ala Lys His Ile Tyr Leu Val Gly His Ser Gln Gly Gly
            100                 105                 110

Val Val Ala Ser Met Leu Ala Gly Tyr Tyr Arg Asp Val Ile Glu Lys
        115                 120                 125

Leu Ala Leu Leu Ala Pro Ala Ala Thr Leu Lys Ser Asp Ala Leu Asp
```

-continued

```
    130                 135                 140

Gly Val Cys Gln Gly Ser Thr Tyr Asp Pro Thr His Ile Pro Glu Thr
145                 150                 155                 160

Val Asn Val Ser Gly Phe Glu Val Gly Gly Ala Tyr Phe Arg Thr Ala
                165                 170                 175

Gln Leu Leu Pro Ile Tyr Gln Thr Ala Glu His Tyr Asn Arg Glu Thr
            180                 185                 190

Leu Leu Ile His Gly Leu Ala Asp Lys Val Val Ser Pro Asn Ala Ser
        195                 200                 205

Arg Lys Phe His Thr Leu Leu Pro Lys Ser Glu Leu His Leu Ile Pro
    210                 215                 220

Asp Glu Gly His Met Phe Asn Gly Lys Asn Arg Pro Glu Val Leu Lys
225                 230                 235                 240

Leu Val Gly Glu Phe Leu Ile Lys
                245


<210> SEQ ID NO 9
<211> LENGTH: 326
<212> TYPE: PRT
<213> ORGANISM: Medicago truncatula
<220> FEATURE:
<223> OTHER INFORMATION: MtCSE

<400> SEQUENCE: 9

Met Ala Thr Gln Gln Glu Ser Glu Ile Pro Pro Asn Phe Trp Gly His
1               5                   10                  15

Thr Pro Glu Glu Glu Tyr Tyr Thr Ser Gln Gly Val Arg Asn Thr Lys
            20                  25                  30

Ser His Phe Glu Thr Pro Asn Gly Lys Ile Phe Thr Gln Ser Phe Leu
        35                  40                  45

Pro Leu Asn Ala Glu Ile Lys Ala Thr Val Tyr Met Thr His Gly Tyr
    50                  55                  60

Gly Ser Asp Thr Gly Trp Leu Phe Gln Lys Ile Cys Ile Thr Tyr Ala
65                  70                  75                  80

Thr Trp Gly Tyr Ala Val Phe Thr Ala Asp Leu Leu Gly His Gly Arg
                85                  90                  95

Ser Asp Gly Leu Arg Cys Tyr Leu Gly Asp Met Asp Lys Ile Ala Ala
            100                 105                 110

Thr Ser Leu Ser Phe Phe Leu His Val Arg Arg Ser Pro Pro Tyr Asn
        115                 120                 125

His Leu Pro Ala Phe Leu Phe Gly Glu Ser Met Gly Gly Leu Ala Thr
    130                 135                 140

Leu Leu Met Tyr Phe Gln Ser Glu Pro Asp Thr Trp Thr Gly Leu Ile
145                 150                 155                 160

Phe Ser Ala Pro Leu Phe Val Ile Pro Glu Asp Met Lys Pro Ser Lys
                165                 170                 175

Ile His Leu Phe Val Tyr Gly Leu Leu Phe Gly Leu Ala Asp Thr Trp
            180                 185                 190

Ala Ala Met Pro Asp Asn Lys Met Val Gly Lys Ala Ile Arg Asp Pro
        195                 200                 205

Asn Lys Leu Lys Ile Ile Ala Ser Asn Pro Arg Arg Tyr Thr Gly Pro
    210                 215                 220

Pro Arg Val Gly Thr Met Arg Glu Leu Leu Arg Val Thr Gln Tyr Val
225                 230                 235                 240

Gln Asp Asn Phe Cys Asn Val Thr Val Pro Phe Leu Thr Ala His Gly
```

-continued

```
                245                 250                 255

Thr Ala Asp Gly Val Thr Cys Pro Ser Ser Ser Lys Leu Leu Tyr Glu
            260                 265                 270

Lys Ala Glu Ser Lys Asp Lys Thr Leu Lys Leu Tyr Glu Gly Met Tyr
        275                 280                 285

His Ser Leu Ile Gln Gly Glu Pro Asp Glu Ser Ala Asn Leu Val Leu
    290                 295                 300

Arg Asp Met Arg Glu Trp Ile Asp Glu Arg Val Arg Arg Tyr Gly Pro
305                 310                 315                 320

Asn Asn Asp Asn Ser Gln
                325


<210> SEQ ID NO 10
<211> LENGTH: 536
<212> TYPE: PRT
<213> ORGANISM: Populus tomentosa
<220> FEATURE:
<223> OTHER INFORMATION: Pt4CL

<400> SEQUENCE: 10

Met Asn Pro Gln Glu Glu Phe Ile Phe Arg Ser Lys Leu Pro Asp Ile
1               5                   10                  15

Tyr Ile Pro Lys Asn Leu Pro Leu His Ser Tyr Val Leu Glu Asn Leu
            20                  25                  30

Ser Asn His Ser Ser Lys Pro Cys Leu Ile Asn Gly Ala Asn Gly Asp
        35                  40                  45

Val Tyr Thr Tyr Ala Asp Val Glu Leu Thr Ala Arg Arg Val Ala Ser
    50                  55                  60

Gly Leu Asn Lys Ile Gly Ile Gln Gln Gly Asp Val Ile Met Leu Phe
65                  70                  75                  80

Leu Pro Ser Ser Pro Glu Phe Val Leu Ala Phe Leu Gly Ala Ser His
                85                  90                  95

Arg Gly Ala Ile Ile Thr Ala Ala Asn Pro Phe Ser Thr Pro Ala Glu
            100                 105                 110

Leu Ala Lys His Ala Lys Ala Ser Arg Ala Lys Leu Leu Ile Thr Gln
        115                 120                 125

Ala Cys Tyr Tyr Glu Lys Val Lys Asp Phe Ala Arg Glu Ser Asp Val
    130                 135                 140

Lys Val Met Cys Val Asp Ser Ala Pro Asp Gly Cys Leu His Phe Ser
145                 150                 155                 160

Glu Leu Thr Gln Ala Asp Glu Asn Glu Ala Pro Gln Val Asp Ile Ser
                165                 170                 175

Pro Asp Asp Val Val Ala Leu Pro Tyr Ser Ser Gly Thr Thr Gly Leu
            180                 185                 190

Pro Lys Gly Val Met Leu Thr His Lys Gly Leu Ile Thr Ser Val Ala
        195                 200                 205

Gln Gln Val Asp Gly Asp Asn Pro Asn Leu Tyr Phe His Ser Glu Asp
    210                 215                 220

Val Ile Leu Cys Val Leu Pro Met Phe His Ile Tyr Ala Leu Asn Ser
225                 230                 235                 240

Ile Met Leu Cys Gly Leu Arg Val Gly Ala Pro Ile Leu Ile Met Pro
                245                 250                 255

Lys Phe Glu Ile Gly Ser Leu Leu Gly Leu Ile Glu Lys Tyr Lys Val
            260                 265                 270

Ser Ile Ala Pro Val Val Pro Pro Val Met Met Ser Ile Ala Lys Ser
```

-continued

```
        275                 280                 285

Pro Asp Leu Asp Lys His Asp Leu Ser Ser Leu Arg Met Ile Lys Ser
    290                 295                 300

Gly Gly Ala Pro Leu Gly Lys Glu Leu Glu Asp Thr Val Arg Ala Lys
305                 310                 315                 320

Phe Pro Gln Ala Arg Leu Gly Gln Gly Tyr Gly Met Thr Glu Ala Gly
                325                 330                 335

Pro Val Leu Ala Met Cys Leu Ala Phe Ala Lys Glu Pro Phe Asp Ile
            340                 345                 350

Lys Pro Gly Ala Cys Gly Thr Val Val Arg Asn Ala Glu Met Lys Ile
        355                 360                 365

Val Asp Pro Glu Thr Gly Ala Ser Leu Pro Arg Asn Gln Pro Gly Glu
    370                 375                 380

Ile Cys Ile Arg Gly Asp Gln Ile Met Lys Gly Tyr Leu Asn Asp Pro
385                 390                 395                 400

Glu Ala Thr Ser Arg Thr Ile Asp Lys Glu Gly Trp Leu His Thr Gly
                405                 410                 415

Asp Ile Gly Tyr Ile Asp Asp Asp Glu Leu Phe Ile Val Asp Arg
            420                 425                 430

Leu Lys Glu Leu Ile Lys Tyr Lys Gly Phe Gln Val Ala Pro Ala Glu
        435                 440                 445

Leu Glu Ala Leu Leu Ile Ala His Pro Glu Ile Ser Asp Ala Ala Val
    450                 455                 460

Val Gly Leu Lys Asp Glu Asp Ala Gly Glu Val Pro Val Ala Phe Val
465                 470                 475                 480

Val Lys Ser Glu Lys Ser Gln Ala Thr Glu Asp Glu Ile Lys Gln Tyr
                485                 490                 495

Ile Ser Lys Gln Val Ile Phe Tyr Lys Arg Ile Lys Arg Val Phe Phe
            500                 505                 510

Ile Glu Ala Ile Pro Lys Ala Pro Ser Gly Lys Ile Leu Arg Lys Asn
        515                 520                 525

Leu Lys Glu Lys Leu Ala Gly Ile
    530                 535


<210> SEQ ID NO 11
<211> LENGTH: 384
<212> TYPE: PRT
<213> ORGANISM: Saccharomyces cerevisiae S288c
<220> FEATURE:
<223> OTHER INFORMATION: SAM2

<400> SEQUENCE: 11

Met Ser Lys Ser Lys Thr Phe Leu Phe Thr Ser Glu Ser Val Gly Glu
1               5                   10                  15

Gly His Pro Asp Lys Ile Cys Asp Gln Val Ser Asp Ala Ile Leu Asp
            20                  25                  30

Ala Cys Leu Glu Gln Asp Pro Phe Ser Lys Val Ala Cys Glu Thr Ala
        35                  40                  45

Ala Lys Thr Gly Met Ile Met Val Phe Gly Glu Ile Thr Thr Lys Ala
    50                  55                  60

Arg Leu Asp Tyr Gln Gln Ile Val Arg Asp Thr Ile Lys Lys Ile Gly
65                  70                  75                  80

Tyr Asp Asp Ser Ala Lys Gly Phe Asp Tyr Lys Thr Cys Asn Val Leu
                85                  90                  95

Val Ala Ile Glu Gln Gln Ser Pro Asp Ile Ala Gln Gly Leu His Tyr
```

-continued

```
            100                 105                 110

Glu Lys Ser Leu Glu Asp Leu Gly Ala Gly Asp Gln Gly Ile Met Phe
        115                 120                 125

Gly Tyr Ala Thr Asp Glu Thr Pro Glu Gly Leu Pro Leu Thr Ile Leu
    130                 135                 140

Leu Ala His Lys Leu Asn Met Ala Met Ala Asp Ala Arg Arg Asp Gly
145                 150                 155                 160

Ser Leu Pro Trp Leu Arg Pro Asp Thr Lys Thr Gln Val Thr Val Glu
                165                 170                 175

Tyr Glu Asp Asp Asn Gly Arg Trp Val Pro Lys Arg Ile Asp Thr Val
            180                 185                 190

Val Ile Ser Ala Gln His Ala Asp Glu Ile Ser Thr Ala Asp Leu Arg
        195                 200                 205

Thr Gln Leu Gln Lys Asp Ile Val Glu Lys Val Ile Pro Lys Asp Met
    210                 215                 220

Leu Asp Glu Asn Thr Lys Tyr Phe Ile Gln Pro Ser Gly Arg Phe Val
225                 230                 235                 240

Ile Gly Gly Pro Gln Gly Asp Ala Gly Leu Thr Gly Arg Lys Ile Ile
                245                 250                 255

Val Asp Ala Tyr Gly Gly Ala Ser Ser Val Gly Gly Gly Ala Phe Ser
            260                 265                 270

Gly Lys Asp Tyr Ser Lys Val Asp Arg Ser Ala Ala Tyr Ala Ala Arg
        275                 280                 285

Trp Val Ala Lys Ser Leu Val Ala Ala Gly Leu Cys Lys Arg Val Gln
    290                 295                 300

Val Gln Phe Ser Tyr Ala Ile Gly Ile Ala Glu Pro Leu Ser Leu His
305                 310                 315                 320

Val Asp Thr Tyr Gly Thr Ala Thr Lys Ser Asp Asp Glu Ile Ile Glu
                325                 330                 335

Ile Ile Lys Lys Asn Phe Asp Leu Arg Pro Gly Val Leu Val Lys Glu
            340                 345                 350

Leu Asp Leu Ala Arg Pro Ile Tyr Leu Pro Thr Ala Ser Tyr Gly His
        355                 360                 365

Phe Thr Asn Gln Glu Tyr Ser Trp Glu Lys Pro Lys Lys Leu Glu Phe
    370                 375                 380


<210> SEQ ID NO 12
<211> LENGTH: 522
<212> TYPE: PRT
<213> ORGANISM: Streptomyces coelicolor
<220> FEATURE:
<223> OTHER INFORMATION: Sc4CL

<400> SEQUENCE: 12

Met Phe Arg Ser Glu Tyr Ala Asp Val Pro Pro Val Asp Leu Pro Ile
1               5                   10                  15

His Asp Ala Val Leu Gly Gly Ala Ala Ala Phe Gly Ser Thr Pro Ala
            20                  25                  30

Leu Ile Asp Gly Thr Asp Gly Thr Thr Leu Thr Tyr Glu Gln Val Asp
        35                  40                  45

Arg Phe His Arg Arg Val Ala Ala Ala Leu Ala Glu Thr Gly Val Arg
    50                  55                  60

Lys Gly Asp Val Leu Ala Leu His Ser Pro Asn Thr Val Ala Phe Pro
65                  70                  75                  80

Leu Ala Phe Tyr Ala Ala Thr Arg Ala Gly Ala Ser Val Thr Thr Val
```

-continued

```
                85                  90                  95

His Pro Leu Ala Thr Ala Glu Glu Phe Ala Lys Gln Leu Lys Asp Ser
            100                 105                 110

Ala Ala Arg Trp Ile Val Thr Val Ser Pro Leu Leu Ser Thr Ala Arg
        115                 120                 125

Arg Ala Ala Glu Leu Ala Gly Gly Val Gln Glu Ile Leu Val Cys Asp
    130                 135                 140

Ser Ala Pro Gly His Arg Ser Leu Val Asp Met Leu Ala Ser Thr Ala
145                 150                 155                 160

Pro Glu Pro Ser Val Ala Ile Asp Pro Ala Glu Asp Val Ala Ala Leu
            165                 170                 175

Pro Tyr Ser Ser Gly Thr Thr Gly Thr Pro Lys Gly Val Met Leu Thr
            180                 185                 190

His Arg Gln Ile Ala Thr Asn Leu Ala Gln Leu Glu Pro Ser Met Pro
        195                 200                 205

Ser Ala Pro Gly Asp Arg Val Leu Ala Val Leu Pro Phe Phe His Ile
    210                 215                 220

Tyr Gly Leu Thr Ala Leu Met Asn Ala Pro Leu Arg Leu Gly Ala Thr
225                 230                 235                 240

Val Val Val Leu Pro Arg Phe Asp Leu Glu Gln Phe Leu Ala Ala Ile
            245                 250                 255

Gln Asn His Arg Ile Thr Ser Leu Tyr Val Ala Pro Pro Ile Val Leu
            260                 265                 270

Ala Leu Ala Lys His Pro Leu Val Ala Asp Tyr Asp Leu Ser Ser Leu
        275                 280                 285

Arg Tyr Ile Val Ser Ala Ala Ala Pro Leu Asp Ala Arg Leu Ala Ala
    290                 295                 300

Ala Cys Ser Gln Arg Leu Gly Leu Pro Pro Val Gly Gln Ala Tyr Gly
305                 310                 315                 320

Met Thr Glu Leu Ser Pro Gly Thr His Val Val Pro Leu Asp Ala Met
            325                 330                 335

Ala Asp Ala Pro Pro Gly Thr Val Gly Arg Leu Ile Ala Gly Thr Glu
            340                 345                 350

Met Arg Ile Val Ser Leu Thr Asp Pro Gly Thr Asp Leu Pro Ala Gly
        355                 360                 365

Glu Ser Gly Glu Ile Leu Ile Arg Gly Pro Gln Ile Met Lys Gly Tyr
    370                 375                 380

Leu Gly Arg Pro Asp Ala Thr Ala Ala Met Ile Asp Glu Glu Gly Trp
385                 390                 395                 400

Leu His Thr Gly Asp Val Gly His Val Asp Ala Asp Gly Trp Leu Phe
            405                 410                 415

Val Val Asp Arg Val Lys Glu Leu Ile Lys Tyr Lys Gly Phe Gln Val
            420                 425                 430

Ala Pro Ala Glu Leu Glu Ala His Leu Leu Thr His Pro Gly Val Ala
        435                 440                 445

Asp Ala Ala Val Val Gly Ala Tyr Asp Asp Asp Gly Asn Glu Val Pro
    450                 455                 460

His Ala Phe Val Val Arg Gln Pro Ala Ala Pro Gly Leu Ala Glu Ser
465                 470                 475                 480

Glu Ile Met Met Tyr Val Ala Glu Arg Val Ala Pro Tyr Lys Arg Val
            485                 490                 495

Arg Arg Val Thr Phe Val Asp Ala Val Pro Arg Ala Ala Ser Gly Lys
            500                 505                 510
```

```
Ile Leu Arg Arg Gln Leu Arg Glu Pro Arg
        515                 520


<210> SEQ ID NO 13
<211> LENGTH: 284
<212> TYPE: PRT
<213> ORGANISM: Salinibacter ruber
<220> FEATURE:
<223> OTHER INFORMATION: SrChlE

<400> SEQUENCE: 13

Met Pro Pro Ser Gly Glu Thr Gly Thr Phe Arg Thr His Asp Gly Leu
1               5                   10                  15

Ser Leu Ala Thr Arg Arg Trp Thr Pro Ser Ala Ala Pro Glu Ala His
            20                  25                  30

Val Leu Leu Val His Gly Tyr Ala Glu His Cys Gly Arg Tyr Asp His
        35                  40                  45

Val Ala Thr Ala Leu Thr Glu Gln Gly Ala Ala Val His Ala Cys Asp
    50                  55                  60

Gln Arg Gly His Gly Arg Ser Asp Gly Arg Arg Ala Tyr Val Asp Arg
65                  70                  75                  80

Phe Glu Gln Tyr Leu Ala Asp Leu Asp Ala Phe Arg Leu His Val Ala
                85                  90                  95

Pro Pro Glu Asp Lys Pro Val Phe Leu Phe Gly His Ser Met Gly Gly
            100                 105                 110

Leu Val Thr Val Leu Tyr Val Leu Asn Arg Arg Pro His Val Asp Gly
        115                 120                 125

Leu Leu Leu Ser Ala Pro Ala Ile Glu Val Asn Pro Asp Leu Ala Pro
    130                 135                 140

Val Leu Arg Arg Met Ala Gln Ala Leu Gly Arg Val Ala Pro Thr Leu
145                 150                 155                 160

Pro Thr Val Arg Ser Pro Gln Gly Ser Ile Ser Arg Asp Pro Ala Val
                165                 170                 175

Leu Glu Asp Ala Arg Asn Asp Pro Leu Asn Tyr His Gly Arg Thr Leu
            180                 185                 190

Ala Arg Thr Gly Ala Glu Leu Leu Arg Ala Gly Asn Asp Ala Gln Arg
        195                 200                 205

Arg Leu His Glu Leu Thr Ile Pro Phe Leu Val Phe His Gly Thr Ala
    210                 215                 220

Asp Pro Leu Val Ser Pro Ala Gly Ser Arg His Leu His Glu Arg Ala
225                 230                 235                 240

Ala Ala Pro Asp Lys Thr Leu Lys Leu Tyr Asp Gly Leu Tyr His Glu
                245                 250                 255

Thr Phe Asn Glu Pro Glu Arg Glu Arg Val Leu Gly Asp Val Ser Thr
            260                 265                 270

Trp Leu Ala Glu Arg Leu Pro Thr Asp Pro Ala Arg
        275                 280


<210> SEQ ID NO 14
<211> LENGTH: 693
<212> TYPE: PRT
<213> ORGANISM: Rhodotorula glutinis
<220> FEATURE:
<223> OTHER INFORMATION: TAL

<400> SEQUENCE: 14

Met Ala Pro Arg Pro Thr Ser Gln Ser Gln Ala Arg Thr Cys Pro Thr
```

-continued

```
1               5                   10                  15

Thr Gln Val Thr Gln Val Asp Ile Val Glu Lys Met Leu Ala Ala Pro
            20                  25                  30

Thr Asp Ser Thr Leu Glu Leu Asp Gly Tyr Ser Leu Asn Leu Gly Asp
        35                  40                  45

Val Val Ser Ala Ala Arg Lys Gly Arg Pro Val Arg Val Lys Asp Ser
    50                  55                  60

Asp Glu Ile Arg Ser Lys Ile Asp Lys Ser Val Glu Phe Leu Arg Ser
65                  70                  75                  80

Gln Leu Ser Met Ser Val Tyr Gly Val Thr Thr Gly Phe Gly Gly Ser
                85                  90                  95

Ala Asp Thr Arg Thr Glu Asp Ala Ile Ser Leu Gln Lys Ala Leu Leu
            100                 105                 110

Glu His Gln Leu Cys Gly Val Leu Pro Ser Ser Phe Asp Ser Phe Arg
        115                 120                 125

Leu Gly Arg Gly Leu Glu Asn Ser Leu Pro Leu Glu Val Val Arg Gly
    130                 135                 140

Ala Met Thr Ile Arg Val Asn Ser Leu Thr Arg Gly His Ser Ala Val
145                 150                 155                 160

Arg Leu Val Val Leu Glu Ala Leu Thr Asn Phe Leu Asn His Gly Ile
                165                 170                 175

Thr Pro Ile Val Pro Leu Arg Gly Thr Ile Ser Ala Ser Gly Asp Leu
            180                 185                 190

Ser Pro Leu Ser Tyr Ile Ala Ala Ala Ile Ser Gly His Pro Asp Ser
        195                 200                 205

Lys Val His Val Val His Glu Gly Lys Glu Lys Ile Leu Tyr Ala Arg
    210                 215                 220

Glu Ala Met Ala Leu Phe Asn Leu Glu Pro Val Val Leu Gly Pro Lys
225                 230                 235                 240

Glu Gly Leu Gly Leu Val Asn Gly Thr Ala Val Ser Ala Ser Met Ala
                245                 250                 255

Thr Leu Ala Leu His Asp Ala His Met Leu Ser Leu Leu Ser Gln Ser
            260                 265                 270

Leu Thr Ala Met Thr Val Glu Ala Met Val Gly His Ala Gly Ser Phe
        275                 280                 285

His Pro Phe Leu His Asp Val Thr Arg Pro His Pro Thr Gln Ile Glu
    290                 295                 300

Val Ala Gly Asn Ile Arg Lys Leu Leu Glu Gly Ser Arg Phe Ala Val
305                 310                 315                 320

His His Glu Glu Glu Val Lys Val Lys Asp Asp Glu Gly Ile Leu Arg
                325                 330                 335

Gln Asp Arg Tyr Pro Leu Arg Thr Ser Pro Gln Trp Leu Gly Pro Leu
            340                 345                 350

Val Ser Asp Leu Ile His Ala His Ala Val Leu Thr Ile Glu Ala Gly
        355                 360                 365

Gln Ser Thr Thr Asp Asn Pro Leu Ile Asp Val Glu Asn Lys Thr Ser
    370                 375                 380

His His Gly Gly Asn Phe Gln Ala Ala Ala Val Ala Asn Thr Met Glu
385                 390                 395                 400

Lys Thr Arg Leu Gly Leu Ala Gln Ile Gly Lys Leu Asn Phe Thr Gln
                405                 410                 415

Leu Thr Glu Met Leu Asn Ala Gly Met Asn Arg Gly Leu Pro Ser Cys
            420                 425                 430
```

-continued

```
Leu Ala Ala Glu Asp Pro Ser Leu Ser Tyr His Cys Lys Gly Leu Asp
        435                 440                 445

Ile Ala Ala Ala Ala Tyr Thr Ser Glu Leu Gly His Leu Ala Asn Pro
    450                 455                 460

Val Thr Thr His Val Gln Pro Ala Glu Met Ala Asn Gln Ala Val Asn
465                 470                 475                 480

Ser Leu Ala Leu Ile Ser Ala Arg Arg Thr Thr Glu Ser Asn Asp Val
                485                 490                 495

Leu Ser Leu Leu Leu Ala Thr His Leu Tyr Cys Val Leu Gln Ala Ile
            500                 505                 510

Asp Leu Arg Ala Ile Glu Phe Glu Phe Lys Lys Gln Phe Gly Pro Ala
        515                 520                 525

Ile Val Ser Leu Ile Asp Gln His Phe Gly Ser Ala Met Thr Gly Ser
    530                 535                 540

Asn Leu Arg Asp Glu Leu Val Glu Lys Val Asn Lys Thr Leu Ala Lys
545                 550                 555                 560

Arg Leu Glu Gln Thr Asn Ser Tyr Asp Leu Val Pro Arg Trp His Asp
                565                 570                 575

Ala Phe Ser Phe Ala Ala Gly Thr Val Val Glu Val Leu Ser Ser Thr
            580                 585                 590

Ser Leu Ser Leu Ala Ala Val Asn Ala Trp Lys Val Ala Ala Ala Glu
        595                 600                 605

Ser Ala Ile Ser Leu Thr Arg Gln Val Arg Glu Thr Phe Trp Ser Ala
    610                 615                 620

Ala Ser Thr Ser Ser Pro Ala Leu Ser Tyr Leu Ser Pro Arg Thr Gln
625                 630                 635                 640

Ile Leu Tyr Ala Phe Val Arg Glu Glu Leu Gly Val Lys Ala Arg Arg
                645                 650                 655

Gly Asp Val Phe Leu Gly Lys Gln Glu Val Thr Ile Gly Ser Asn Val
            660                 665                 670

Ser Lys Ile Tyr Glu Ala Ile Lys Ser Gly Arg Ile Asn Asn Val Leu
        675                 680                 685

Leu Lys Met Leu Ala
    690


<210> SEQ ID NO 15
<211> LENGTH: 585
<212> TYPE: PRT
<213> ORGANISM: Ustilago maydis
<220> FEATURE:
<223> OTHER INFORMATION: UmChlE

<400> SEQUENCE: 15

Met Arg Leu Pro Asn Leu Thr Leu Leu Val Trp Ala Ala Thr Ser Val
1               5                   10                  15

Gly Leu Val Ser Ala Leu Pro Gln Val Ser Tyr Lys Ala Asp Ala Thr
            20                  25                  30

Ala Ser Ala Pro Thr Val Lys Leu His Gln Gly Thr Val Arg Gly Leu
        35                  40                  45

Ala Asp Asp Asn Tyr Gly Leu Glu Gln Phe Phe Gly Ile Pro Tyr Ala
    50                  55                  60

Lys Pro Pro Val Gly Ser Leu Arg Phe Ala Lys Pro Gln Pro Leu Gly
65                  70                  75                  80

Pro Ala Ser Ser His Lys Thr Val Ile Asp Ala Thr Arg Phe Gly Asp
                85                  90                  95
```

-continued

```
Ile Cys Met Gln Thr Val Ala Pro Ser Pro Leu Tyr Asn Met Ser Glu
            100                 105                 110

Asp Cys Leu Asn Leu Asn Val Val Arg Pro Lys Gly Thr Thr Ala Lys
        115                 120                 125

Asp Lys Leu Pro Val Leu Val Trp Ile Tyr Gly Gly Ala Phe Arg Gln
    130                 135                 140

Gly Ser Thr Pro Ile Tyr Asn Ala Ser Glu Leu Val Gln Lys Ser Val
145                 150                 155                 160

Glu Ile Gly Lys Pro Ile Val Phe Val Ala Ile Ser Tyr Arg Val Gly
                165                 170                 175

Pro Phe Gly Phe Ile Gly Gly Ser Glu Ile Ala Asp Ser Asp Ser Ala
            180                 185                 190

Thr Ser Asn Ala Gly Leu Tyr Asp Gln Arg Leu Gly Leu Lys Trp Ile
        195                 200                 205

Arg His Asn Ile Gly Lys Phe Gly Gly Asp Lys Asn Arg Val Thr Leu
    210                 215                 220

Phe Gly Gln Ser Ala Gly Ala Met Ser Ile Ala Leu Gln Asn Phe Ala
225                 230                 235                 240

Tyr Asp Gly Asn Asn His Gly Leu Trp His Ala Ala Ile Met Asn Ser
                245                 250                 255

Gly Gly Ile Ala Pro Gly Pro Leu Leu Thr Pro Lys His Pro Thr Val
            260                 265                 270

Glu Gln Ser Phe Lys Arg Leu Ala Asn Gly Val Gly Cys Thr Gly Gly
        275                 280                 285

Ser Leu Leu Arg Cys Leu Arg Lys Ala Asn Ala Ser Glu Val Gln Thr
    290                 295                 300

Val Ala Ser Asn Leu Thr Ala Gln Ala Gly Gly Thr Phe Pro Ile Pro
305                 310                 315                 320

Gly Ala Leu Ala Trp Leu Pro Leu Val Asp Tyr Glu Leu Ile Thr Asn
                325                 330                 335

Tyr Pro Ser Val Asn Leu Pro Gln Gly Lys Leu Ala Asp Ile Pro Val
            340                 345                 350

Ile Gln Gly Asn Ala Leu Asp Glu Gly Thr Ser Phe Ala Gln Lys Gln
        355                 360                 365

Leu Asn Ser Ser Ala Asp Phe Glu Arg Trp Val Arg Ser Ala Ala Val
    370                 375                 380

Ile His Asn Thr Ser Tyr Thr Glu Gln Ala Leu Gln Lys Val Phe Glu
385                 390                 395                 400

Leu Tyr Pro Asp Val Pro Glu Gln Gly Ser Pro Phe Tyr Asn Ala Glu
                405                 410                 415

Thr Ala Thr Ser Ala Ala Thr Thr Ser Asp Leu Asn Ser Arg Gln Tyr
            420                 425                 430

Pro Pro Leu Thr Ser Asn Gln Tyr Lys Arg Ser Ala Ala Phe Phe Gly
        435                 440                 445

Asp Phe Thr Phe Gln Ala Gln Arg Arg Thr Tyr Leu Lys Ala Ala Thr
    450                 455                 460

Leu Gly Trp Lys Lys Asn Lys Ala Lys Val Trp Ser Tyr Glu Phe Gln
465                 470                 475                 480

Gln Asn Asp Lys Phe Ala Asn Gly Thr Gly Ser Leu Leu Gly Pro Tyr
                485                 490                 495

His Gly Ala Asp Val Lys Tyr Tyr Phe Ile Arg Pro Asp Gly Arg Gln
            500                 505                 510
```

-continued

```
Lys Asp Pro Val Leu Ala Asp Arg Met Pro Arg Ala Tyr Ile Ser Phe
        515                 520                 525

Val Tyr His His Asp Pro Thr Val Leu Gly Gly Phe Glu Trp Pro Pro
    530                 535                 540

Tyr Gly Lys Gly Lys Lys Leu Leu Gln Met Lys Gly Asp Asn Thr Thr
545                 550                 555                 560

Val Ile Glu Asp Ala Tyr Arg Lys Glu Ala Met Asp Ala Leu Thr Asn
                565                 570                 575

Arg Lys Ala Ala Lys Val Phe Gly Phe
            580                 585
```

RECOMBINANT YEAST CAPABLE OF PRODUCING CAFFEIC ACID AND/OR FERULIC ACID

CROSS-REFERENCE TO RELATED PATENT APPLICATIONS

This application is a U.S. National Stage Application under 35 U.S.C. § 371 of International Patent Application No. PCT/FR2020/052021 filed Nov. 6, 2020, which claims the benefit of priority of French Patent Application No. 1912573 filed Nov. 8, 2019, both of which are incorporated by reference in their entireties. The International Application was published on May 14, 2021, as International Publication No. WO/2021/089961 A1.

FIELD OF THE INVENTION

The present invention relates to a recombinant microorganism, preferably a recombinant yeast, capable of producing caffeic acid comprising a heterologous gene coding for an enzyme of the hydrolase family capable of breaking, preferably of hydrolyzing, the caffeoyl-shikimate bond to produce caffeic acid from caffeoyl-shikimate. Said microorganism, preferably said recombinant yeast, may also be capable of producing ferulic acid from the caffeic acid obtained. The present invention also relates to a method for producing caffeic acid and a method for producing caffeic acid and/or ferulic acid, using microorganisms, preferably yeasts, according to the invention. Finally, the invention also relates to the use of microorganisms, preferably yeasts, according to the invention to produce caffeic acid and/or ferulic acid.

STATE OF THE ART

Ferulic acid is an organic hydroxycinnamic acid present in many plants, and involved in the synthesis of lignin. This molecule is used in many applications. In the cosmetic and therapeutic field, ferulic acid is known for its antioxidant properties because it reacts with free radicals such as reactive oxygen species. Research is also carried out on applications in Alzheimer's disease, cardiovascular diseases, diabetes, atherosclerosis, coronary diseases, inflammatory pathologies or even cancers. Apart from these applications in human health, ferulic acid is also used in food for its preservative antimicrobial properties, and as a precursor in the manufacture of vanillin, a flavoring agent often used in place of the natural extract of vanilla. By virtue of its properties, the production of ferulic acid is thus a constantly growing need.

Caffeic acid is a precursor to ferulic acid, which is synthesized in plants as an intermediate in lignin synthesis as well. This molecule is mainly used for its anti-inflammatory, antiviral, anti-cancer and antioxidant properties.

Today, ferulic acid is mainly recovered by chemical hydrolysis of lignocellulosic biomasses. However, the extraction yield of this method is relatively low and consequently entails a particularly high production cost of ferulic acid per kilogram.

The production of ferulic acid has in fact been considered in *Escherichia coli*, but although the production rates of the pathway intermediates are high, the final yield of ferulic acid production remains limited (Kang S.-Y., Choi O., Lee K. J., Hwang B. Y., Uhm T.-B., Hong Y. S. 2012. Artificial biosynthesis of phenylpropanoic acids in a tyrosine overproducing *Escherichia coli* strain. Microbial Cell Factories 11:153.).

Caffeic acid is also extracted from plant materials, which, in the same way as for ferulic acid, leads to low yield and high production costs.

A caffeic acid production pathway has been described in yeast (Liu L., Liu H., Zhang W., Yao M., Li B., Liu D., Yuan Y. 2019. Engineering the biosynthesis of caffeic acid in *Saccharomyces cerevisiae* with heterologous enzyme combinations. Engineering 5: 287-295). It consists of the direct conversion of p-coumaric acid into caffeic acid via a single hydroxylation step. However, the hydroxylases used in these studies, SAM5 (Zhang H., Stephanopoulos G. 2012. Engineering *E. coli* for caffeic acid biosynthesis from renewable sugars. Applied Microbiology and Biotechnology 97:3333-3341), COUM3H, HpaBC (Furuya T. & Kino K. 2014. Catalytic activity of the two-component flavin-dependent monooxygenase from *Pseudomonas aeruginosa* toward cinnamic acid derivatives. Appl Microbiol Biotechnol 98:1145-1154.) and Cyp199A2 (Furuya T. & Kino K. 2014. Catalytic activity of the two-component flavin-dependent monooxygenase from *Pseudomonas aeruginosa* toward cinnamic acid derivatives. Appl Microbiol Biotechnol 98:1145-1154), are relatively ineffective in yeast, suggesting a low production yield.

Thus, there remains the need to improve the production yields of caffeic acid and ferulic acid, while lowering their production costs.

The general inventive concept common to this invention is a new method of synthesizing these molecules via an alternative metabolic pathway having caffeoyl-shikimate as the main intermediate in the same recombinant microorganism, preferably the same yeast.

Surprisingly, the Applicant has discovered that a recombinant microorganism, preferably a recombinant yeast, comprising genes from plants, and more particularly from the lignin biosynthetic pathway, allowed caffeic acid and ferulic acid to be produced from glucose in particular, making it possible to increase the production yields of these compounds and to lower the cost thereof.

DISCLOSURE OF THE INVENTION

According to a first aspect, the invention consists of a recombinant microorganism, preferably a recombinant yeast, capable of producing caffeic acid, comprising:

- A heterologous gene coding for an enzyme of the hydrolase family capable of breaking, preferably of hydrolyzing, the caffeoyl-shikimate bond to produce caffeic acid from caffeoyl-shikimate.

"Microorganism" means a living organism of microscopic size, in particular bacteria or unicellular fungi such as yeasts, or any prokaryotic or eukaryotic cells.

According to the invention, "recombinant microorganism" means a microorganism that has been genetically modified by the introduction and optionally the modulation of the expression and/or the blocking and/or the inactivation of genes.

Yeasts are unicellular eukaryotic microorganisms of the fungal kingdom.

According to the invention, "recombinant yeast" means a yeast that has been genetically modified by the introduction and optionally the modulation of the expression and/or the blocking and/or the inactivation of genes.

Preferably, the enzyme capable of breaking, preferably hydrolyzing, the caffeoyl-shikimate bond to produce caffeic acid from caffeoyl-shikimate is a caffeoyl-shikimate esterase (CSE).

The reaction performed is depicted in FIG. 1.

Caffeic acid is a phenylpropanoid and acid-phenol present in plants, and acting as an intermediate in the biosynthesis of lignin. The crude chemical formula of caffeic acid is $C_9H_8O_4$ and its molar mass is 180.16 g/mol.

The chemical structure of caffeic acid is:

[Chem 1]

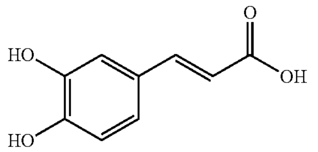

"Heterologous gene" means that the gene has been introduced by genetic engineering into the cell. It can be present there in episomal or chromosomal form. The origin of the gene may be different from the cell into which it is introduced. However, the gene can also come from the same species as the cell into which it is introduced but be considered heterologous due to its unnatural environment. For example, the gene is heterologous because it is under the control of a promoter other than its natural promoter, it is introduced in a place different from where it is naturally located. The host cell may contain a copy of the endogenous gene prior to the introduction of the heterologous gene or it may contain no endogenous copy. Furthermore, the nucleic acid sequence may be heterologous in the sense that the coding sequence has been optimized for expression in the host microorganism.

"Producing caffeic acid" means the obtaining of this compound, including its synthesis, owing to the recombinant microorganism, preferably the recombinant yeast, according to the invention.

"Hydrolase" means an enzyme capable of breaking a covalent bond, preferably by hydrolysis.

"Breaking, preferably hydrolyzing, the caffeoyl-shikimate bond" means the chemical and enzymatic decomposition breaking a covalent bond of this compound enzymatically, preferably by hydrolysis, in order to allow the production of shikimate and caffeic acid.

A caffeoyl-shikimate esterase (CSE) is an enzyme capable of hydrolyzing the caffeoyl-shikimate bond. It exists for example in the lignin biosynthetic pathway (Ha C. M., Escamilla-Trevino L., Yarce J. C. S., Kim H., Ralph J., Chen F., Dixon R. A. 2016. An essential role of caffeoyl shikimate esterase in monolignol biosynthesis in *Medicago truncatula*. Plant J. 86950:363-75; and Vanholme R., Cesarino I., Rataj K., Xiao Y., Sundin L., Goeminne G., Kim H., Cross J., Morreel K., Araujo P., Welsh L., Haustraete J., McClellan C., Vanholme B., Ralph J., Simpson G. G., Halpin C., Boerjan W. 2013. Caffeoyl shikimate esterase (CSE) is an enzyme in the lignin biosynthetic pathway in *Arabidopsis*. Science 341:1103-6.).

Preferably according to the invention, the heterologous gene coding for a CSE is a gene originating from a prokaryotic or eukaryotic organism.

According to one embodiment, the heterologous gene coding for a CSE is the *Medicago truncatula* CSE (MtCSE) gene (XM_003609990.3, Genbank, SEQ ID NO. 9) or a gene coding for a sequence having at least 55, 60, 70, 80, 85, 90 or 95% identity with the amino acid sequence of *Medicago truncatula* CSE (MtCSE) and exhibiting caffeoyl-shikimate esterase activity.

*Medicago truncatula*, or barrel medic, is a species in the family Fabaceae, subfamily Faboideae.

According to one embodiment, the heterologous gene coding for a CSE is the *Arabidopsis thaliana* CSE (AtCSE) gene (At1g52760, GenBank, SEQ ID NO. 3) or a gene coding for a sequence having at least 55, 60, 70, 80, 85, 90 or 95% identity with the amino acid sequence of *Arabidopsis thaliana* CSE (AtCSE) and exhibiting caffeoyl-shikimate esterase activity.

*Arabidopsis thaliana* or mouse-ear cress is a species of the Brassicaceae family.

According to one embodiment, the enzyme capable of breaking, preferably hydrolyzing, the caffeoyl-shikimate bond to produce caffeic acid from caffeoyl-shikimate is a chlorogenic acid esterase (ChlE).

A chlorogenic acid esterase (ChlE) is an enzyme traditionally having chlorogenic acid hydrolysis activity, and used here to hydrolyze the caffeoyl-shikimate bond and thus produce caffeic acid from caffeoyl-shikimate.

According to one embodiment, the heterologous gene for a ChlE is the ChlE gene of *Bifidobacterium animalis* subsp. *Lactis* (BiChlE) (CP001606.1:789353-790141, GenBank, SEQ ID NO. 4) or a gene coding for a sequence having at least 55, 60, 70, 80, 85, 90 or 95% identity with the amino acid sequence of ChlE from *Bifidobacterium animalis* subsp. *Lactis* (BiChlE) and exhibiting chlorogenic acid esterase activity.

*Bifidobacterium animalis* subsp. *Lactis* is a species of lactic acid bacteria isolated from chicken, rabbit and human feces, as well as fermented milk.

According to one embodiment, the heterologous gene for a ChlE is the ChlE gene from *Ustilago maydis* (UmChlE) (HG970190.1, GenBank, SEQ ID NO. 15) or a gene coding for a sequence having at least 55, 60, 70, 80, 85, 90 or 95% identity with the amino acid sequence of *Ustilago maydis* ChlE (UmChlE) and exhibiting chlorogenic acid esterase activity.

*Ustilago maydis* is a pathogenic fungus causing corn smut in particular.

According to one embodiment, the heterologous gene for a ChlE is the ChlE gene of *Lactobacillus johnsonii* (LaChlE) (SPPI01000004.1:37780-38526, GenBank, SEQ ID NO. 8) or a gene coding for a sequence having at least 55, 60, 70, 80, 85, 90 or 95% identity with the amino acid sequence of *Lactobacillus johnsonii* ChlE (LaChlE) and exhibiting chlorogenic acid esterase activity.

*Lactobacillus johnsonii* is a lactic acid bacteria that is part of the healthy vaginal microbiota.

According to one embodiment, the heterologous gene for ChlE is the *Salinibacter ruber* ChlE (SrChlE) gene (CP030369.1:2322200-2323400, GenBank, SEQ ID NO. 13) or a gene coding for a sequence having at least 55, 60, 70, 80, 85, 90 or 95% identity with the amino acid sequence of *Salinibacter ruber* ChlE (SrChlE) and exhibiting chlorogenic acid esterase activity.

*Salinibacter ruber* is a halophilic red bacterium that thrives in a highly concentrated salt environment.

Within the meaning of the present invention, "percentage of identity" between two gene sequences means a percentage of identical nucleotides or amino acid residues between the two sequences to be compared, obtained after the best alignment, this percentage being purely statistical and the differences between the two sequences being randomly distributed over their entire length. The best alignment or optimal alignment is the alignment for which the percentage identity between the two sequences to be compared is the highest.

Preferably according to the invention, said recombinant microorganism, preferably said recombinant yeast, further comprises:

A heterologous gene coding for an enzyme capable of catalyzing the formation of the bond between coumaric acid and coenzyme A.

Preferably, the enzyme capable of catalyzing the formation of the bond between coumaric acid and coenzyme A is a 4-coumarate-CoA ligase (4CL).

According to the invention, "capable of catalyzing the formation of the bond between coumaric acid and coenzyme A" is understood to mean that from these two compounds, the enzyme is capable of producing coumaroyl-CoA. This enzymatic reaction involves ATP and can take place in one or more steps.

A 4-coumarate-CoA ligase (4CL) is an enzyme that catalyzes the formation of coumaroyl-CoA from coumaric acid and coenzyme A.

Preferably according to the invention, the heterologous gene coding for a 4CL is a gene originating from a prokaryotic or eukaryotic organism.

Preferably according to the invention, the heterologous gene coding for said 4CL is mutated in order to reduce the affinity of said mutated 4CL for caffeic acid and to increase its specificity for p-coumaric acid compared to the parent gene coding for an unmutated 4CL.

According to one embodiment, the 4CL is *Populus tomentosa* 4CL (AY043495, Genbank, SEQ ID NO. 10).

*Populus tomentosa*, or Chinese white poplar, is a species of the family Salicaceae.

According to one embodiment, in the case where the 4CL is 4CL from *Populus tomentosa*, the amino acid:

at position 236 is an Alanine (Y236A) or a Phenylalanine (Y236F); and/or at position 240 is an Alanine (S240A); and/or at position 305 is an Alanine (G305A); and/or at position 329 is an Alanine (G329A) According to one embodiment, the 4CL is *Arabidopsis thaliana* 4CL (At1g51680, GenBank, SEQ ID NO. 1).

According to one embodiment, in the case where the 4CL is the 4CL of *Arabidopsis thaliana*, the amino acid:

at position 264 is an Alanine (S264A); and/or at position 329 is an Alanine (G329A); and/or at position 353 is an Alanine (G353A).

Since 4CL is not specific for p-coumaric acid and also accepts caffeic acid as a substrate, the latter released by CSE is likely to be converted back into caffeoyl-CoA by 4CL. These mutations are made to overcome this problem, and reduce the affinity of 4CL for caffeic acid while improving its specificity for p-coumaric acid.

According to one embodiment, the 4CL is *Streptomyces coelicolor* 4CL (CAB95894.1, Genbank, SEQ ID NO. 12).

*Streptomyces coelicolor* is a Gram-positive soil bacterium.

Preferably according to the invention, said recombinant microorganism, preferably said recombinant yeast, further comprises:

A heterologous gene coding for a Hydroxycinnamoyl-Transferase (HCT); and

A heterologous gene coding for a Coumarate 3 Hydroxylase (C3H); and

A heterologous gene coding for a Tyrosine Ammonia Lyase (TAL), and/or a heterologous gene coding for a Phenylalanine Ammonia-Lyase (PAL) and a heterologous gene coding for a Cinnamate 4-Hydroxylase (C4H).

Preferably according to the invention, said recombinant microorganism, preferably said recombinant yeast, further comprises:

A heterologous gene coding for a Cytochrome P450 reductase (CPR1).

According to one embodiment of the invention, said recombinant microorganism, preferably said recombinant yeast, further comprises:

A heterologous gene coding for a Hydroxycinnamoyl-Transferase (HCT); and

A heterologous gene coding for a Coumarate 3 Hydroxylase (C3H); and

A heterologous gene coding for a Tyrosine Ammonia Lyase (TAL), and/or a heterologous gene coding for a Phenylalanine Ammonia-Lyase (PAL) and a heterologous gene coding for a Cinnamate 4-Hydroxylase (C4H); and A heterologous gene coding for a Cytochrome P450 reductase (CPR1).

A Hydroxycinnamoyl-Transferase (HCT) is an enzyme from the transferase family, which catalyzes the reaction: 4-coumaroyl-CoA+shikimate⇆CoA+4-coumaroylshikimate.

Preferably according to the invention, the heterologous gene coding for an HCT is a gene originating from a prokaryotic or eukaryotic organism, preferably *Arabidopsis thaliana* (At5g48930, GenBank, SEQ ID NO. 7).

A Coumarate 3 Hydroxylase (C3H) is an enzyme involved in the synthesis of lignin, and which catalyzes the production of caffeoyl shikimate from coumaroyl shikimate.

Preferably according to the invention, the heterologous gene coding for a C3H is a gene originating from a prokaryotic or eukaryotic organism, preferably *Arabidopsis thaliana* (At2g40890, GenBank, SEQ ID NO. 5).

A Cytochrome P450 reductase (CPR1) is a membrane oxidoreductase which allows the transfer of electrons from NADPH to cytochrome P450.

Preferably according to the invention, the heterologous gene coding for a CPR1 is a gene originating from a prokaryotic or eukaryotic organism, preferably *Catharanthus roseus*(X69791.1, GenBank, SEQ ID NO. 6).

*Catharanthus roseus*, or Madagascar periwinkle, is a plant of the Apocynaceae family native to Madagascar.

A Tyrosine Ammonia Lyase (TAL) is an enzyme that transforms tyrosine into p-coumaric acid with the release of ammonia.

Preferably according to the invention, the heterologous gene coding for a TAL is a gene originating from a prokaryotic or eukaryotic organism, preferably *Rhodotorula glutinis* (KF765779.1, GenBank, SEQ ID NO. 14).

*Rhodotorula glutinis* is a pink yeast from the genus *Rhodotorula*.

A Phenylalanine Ammonia-Lyase (PAL) is an enzyme that catalyzes the transformation of phenylalanine into cinnamic acid, with the release of ammonia.

A Cinnamate 4-Hydroxylase (C4H), or Trans-cinnamate 4-monooxygenase, is an enzyme that transforms trans-cinnamic acid (CA) into p-coumaric acid.

Preferably according to the invention, said recombinant microorganism, preferably said recombinant yeast, further comprises:

A gene coding for a 3-deoxy-7-phosphoheptulonate synthase (ARO4) mutated so that the product is resistant to feedback inhibition compared to the parent gene; and/or A gene coding for a chorismate mutase (ARO7) mutated so that the product is resistant to feedback inhibition compared to the parent gene.

Preferably according to the invention, said recombinant microorganism, preferably said recombinant yeast, further comprises the invalidation for:

a gene coding for a Phenylpyruvate decarboxylase (ARO10).

According to one embodiment of the invention, said recombinant microorganism, preferably said recombinant yeast, further comprises:

A gene coding for a 3-deoxy-7-phosphoheptulonate synthase (ARO4) mutated so that the product is resistant to feedback inhibition compared to the parent gene; and/or A gene coding for a chorismate mutase (ARO7) mutated so that the product is resistant to feedback inhibition compared to the parent gene; and/or invalidation of:

a gene coding for a Phenylpyruvate decarboxylase (ARO10).

"Invalidation" means suppression or inhibition of gene expression, and thus suppression or inhibition of enzyme activity.

A 3-deoxy-7-phosphoheptulonate synthase (ARO4), or DAHP synthase, is a transferase that intervenes in the first step of the shikimate pathway, and which catalyzes the reaction: phosphoenolpyruvate+D-erythrose-4-phosphate+H2O⇆3-deoxy-D-arabinoheptulosonate-7-phosphate+phosphate.

A chorismate mutase (ARO7) is an isomerase that intervenes in the shikimate pathway, and which is known to catalyze a pericyclic reaction. This enzyme catalyzes the reaction: chorismate⇆prephenate.

ARO4 and ARO7 are two genes involved in the de novo synthesis of aromatic amino acids such as phenylalanine and tyrosine in yeast.

Preferably, the ARO4 gene (NP_009808, GenBank) is mutated so that the amino acid at position 229 is Leucine (K229L).

Preferably, the ARO7 gene (NP_015385, GenBank) is mutated so that the amino acid at position 141 is a Serine (G141S).

These mutations of ARO4 and ARO7 have the effect of optimizing an increased production of aromatic amino acids in yeast.

Phenylpyruvate decarboxylase (ARO10) is an enzyme involved in particular in the degradation of phenylalanine and tyrosine in yeast.

Together, the mutations of ARO4 and ARO7 and the invalidation of ARO10 are carried out to optimize an increased production of aromatic amino acids such as phenylalanine and tyrosine.

According to one embodiment, said recombinant microorganism, preferably said recombinant yeast, is capable of producing ferulic acid.

Preferably, said recombinant microorganism, preferably said recombinant yeast, is capable of producing ferulic acid from the caffeic acid obtained, and further comprises:

A heterologous gene coding for a caffeoyl-O-methyl transferase (COMT).

Even more preferably, said recombinant microorganism, preferably said recombinant yeast, capable of producing ferulic acid from the caffeic acid obtained further comprises:

A gene coding for S-Adenosylmethyltransferase (SAM2).

Ferulic acid is an organic hydroxycinnamic acid present in many plants, and involved in the synthesis of lignin.

The crude chemical formula of ferulic acid is $C_{10}H_{10}O_4$ and this compound has a molar mass of 194.18 g/mol.

The chemical structure of ferulic acid is:

[Chem 2]

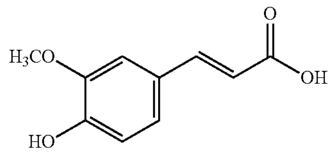

An S-Adenosylmethyltransferase, or S-adenosylmethionine synthase 2 (SAM2), catalyzes the formation of S-adenosylmethionine from methionine and ATP. The reaction comprises two steps catalyzed by the same enzyme: the formation of S-adenosylmethionine and triphosphate and the subsequent hydrolysis of the triphosphate. In the context of the invention, it allows methionine to be transformed into S-adenosylmethionine and into S-adenosilhomocysteine, which allows the methylation of caffeic acid into ferulic acid.

Preferably, the SAM2 gene is the SAM2 gene of *Saccharomyces cerevisiae* and is a copy of the one naturally comprised (YDR502C, SGD Database, SEQ ID NO. 11).

A Caffeoyl-O-methyl Transferase (COMT) is an enzyme that catalyzes the reaction: S-adenosyl-L-methionine+caffeic acid⇆S-adenosyl-L-homocysteine+ferulic acid.

Preferably according to the invention, the heterologous gene coding for COMT is a gene originating from a prokaryotic or eukaryotic organism, preferably *Arabidopsis thaliana* (At5g54160, GenBank, SEQ ID NO. 2).

Preferably, said yeast according to the invention capable of producing ferulic acid further comprises the invalidation of the gene coding for a ferulic acid decarboxylase 1 (FDC1).

A ferulic acid decarboxylase is an enzyme that catalyzes the decarboxylation of aromatic carboxylic acids such as ferulic acid, p-coumaric acid or cinnamic acid, producing the corresponding vinyl derivatives 4-vinylphenol, 4-vinylguaiacol and styrene, respectively, which play the role of aromatic metabolites.

Preferably according to the invention, said recombinant microorganism, preferably said recombinant yeast, is a species of the Ascomycota phylum, preferably chosen from the genera Schizosaccharomycetes, *Saccharomyces, Kluyveromyces, Komagataella, Scheffersomyces, Torulaspora* and/or *Zygosaccharomyces*.

Preferably according to the invention, said recombinant microorganism, preferably said recombinant yeast, is of the *Saccharomyces cerevisiae* species.

*Saccharomyces cerevisiae* is a unicellular eukaryotic yeast, occurring in ovoid to rounded form, approximately 6 to 12 μm in length and 6 to 8 μm in width.

According to an embodiment where all of the genes discussed above are respectively introduced and/or invalidated, the metabolic pathways for the production of caffeic acid and ferulic acid in the yeast according to the invention are illustrated in FIG. 2.

According to a second aspect, the invention relates to a method for modifying a microorganism, preferably a yeast, to produce caffeic acid, comprising the introduction of:

A heterologous gene coding for an enzyme of the hydrolase family capable of breaking, preferably of hydrolyzing, the caffeoyl-shikimate bond to produce caffeic acid from caffeoyl-shikimate.

Preferably, the enzyme capable of breaking, preferably hydrolyzing, the caffeoyl-shikimate bond to produce caffeic acid from caffeoyl-shikimate is a caffeoyl-shikimate esterase (CSE).

Preferably according to the invention, the heterologous gene coding for a CSE is a gene originating from a prokaryotic or eukaryotic organism.

According to one embodiment, the heterologous gene coding for a CSE is the *Medicago truncatula* CSE (MtCSE) gene (XM_003609990.3, Genbank, SEQ ID NO. 9) or a gene coding for a sequence having at least 55, 60, 70, 80, 85, 90 or 95% identity with the amino acid sequence of *Medicago truncatula* CSE (MtCSE) and exhibiting caffeoyl-shikimate esterase activity.

According to one embodiment, the heterologous gene coding for a CSE is the *Arabidopsis thaliana* CSE (AtCSE) gene (At1g52760, GenBank, SEQ ID NO. 3) or a gene coding for a sequence having at least 55, 60, 70, 80, 85, 90 or 95% identity with the amino acid sequence of *Arabidopsis thaliana* CSE (AtCSE) and exhibiting caffeoyl-shikimate esterase activity.

According to one embodiment, the enzyme capable of breaking, preferably hydrolyzing, the caffeoyl-shikimate bond to produce caffeic acid from caffeoyl-shikimate is a chlorogenic acid esterase (ChIE).

According to one embodiment, the heterologous gene for a ChIE is the ChIE gene of *Bifidobacterium animalis* subsp. *Lactis* (BiChIE) (CP001606.1:789353-790141, GenBank, SEQ ID NO. 4) or a gene coding for a sequence having at least 55, 60, 70, 80, 85, 90 or 95% identity with the amino acid sequence of ChIE from *Bifidobacterium animalis* subsp. *Lactis* (BiChIE) and exhibiting chlorogenic acid esterase activity.

According to one embodiment, the heterologous gene for a ChIE is the ChIE gene from *Ustilago maydis* (UmChIE) (HG970190.1, GenBank, SEQ ID NO. 15) or a gene coding for a sequence having at least 55, 60, 70, 80, 85, 90 or 95% identity with the amino acid sequence of *Ustilago maydis* ChIE (UmChIE) and exhibiting chlorogenic acid esterase activity.

According to one embodiment, the heterologous gene for a ChIE is the ChIE gene of *Lactobacillus johnsonii* (LaChIE) (SPP101000004.1:37780-38526, GenBank, SEQ ID NO. 8) or a gene coding for a sequence having at least 55, 60, 70, 80, 85, 90 or 95% identity with the amino acid sequence of *Lactobacillus johnsonii* ChIE (LaChIE) and exhibiting chlorogenic acid esterase activity.

According to one embodiment, the heterologous gene for ChIE is the *Salinibacter ruber* ChIE (SrChIE) gene (CP030369.1:2322200-2323400, GenBank, SEQ ID NO. 13) or a gene coding for a sequence having at least 55, 60, 70, 80, 85, 90 or 95% identity with the amino acid sequence of *Salinibacter ruber* ChIE (SrChIE) and exhibiting chlorogenic acid esterase activity.

Preferably according to the invention, said method of modifying a microorganism, preferably a yeast, to produce caffeic acid further comprises introducing:

A heterologous gene coding for an enzyme capable of catalyzing the formation of the bond between coumaric acid and coenzyme A.

Preferably, the enzyme capable of catalyzing the formation of the bond between coumaric acid and coenzyme A is a 4-coumarate-CoA ligase (4CL).

Preferably according to the invention, the heterologous gene coding for a 4CL is a gene originating from a prokaryotic or eukaryotic organism.

Preferably according to the invention, the heterologous gene coding for a 4CL is mutated in order to reduce the affinity of said mutated 4CL for caffeic acid and to increase its specificity for p-coumaric acid compared to the parent gene coding for an unmutated 4CL.

According to one embodiment, the 4CL is *Populus tomentosa* 4CL (AY043495, Genbank, SEQ ID NO. 10).

According to one embodiment, in the case where the 4CL is 4CL from *Populus tomentosa*, the amino acid:

at position 236 is an Alanine (Y236A) or a Phenylalanine (Y236F); and/or at position 240 is an Alanine (S240A); and/or at position 305 is an Alanine (G305A); and/or at position 329 is an Alanine (G329A) According to one embodiment, the 4CL is *Arabidopsis thaliana* 4CL (At1g51680, GenBank, SEQ ID NO. 1).

According to one embodiment, in the case where the 4CL is the 4CL of *Arabidopsis thaliana*, the amino acid:

at position 264 is an Alanine (S264A); and/or at position 329 is an Alanine (G329A); and/or at position 353 is an Alanine (G353A).

According to one embodiment, the 4CL is *Streptomyces coelicolor* 4CL (CAB95894.1, Genbank, SEQ ID NO. 12).

Preferably according to the invention, said method of modifying a microorganism, preferably a yeast, to produce caffeic acid further comprises introducing:

A heterologous gene coding for a Hydroxycinnamoyl-Transferase (HCT); and

A heterologous gene coding for a Coumarate 3 Hydroxylase (C3H); and

A heterologous gene coding for a Tyrosine Ammonia Lyase (TAL), and/or a heterologous gene coding for a Phenylalanine Ammonia-Lyase (PAL) and a heterologous gene coding for a Cinnamate 4-Hydroxylase (C4H).

Preferably according to the invention, said method of modifying a microorganism, preferably a yeast, to produce caffeic acid further comprises introducing:

A heterologous gene coding for a Cytochrome P450 reductase (CPR1).

According to one embodiment of the invention, said method of modifying a microorganism, preferably a yeast, to produce caffeic acid further comprises introducing:

A heterologous gene coding for a Hydroxycinnamoyl-Transferase (HCT); and

A heterologous gene coding for a Coumarate 3 Hydroxylase (C3H); and

A heterologous gene coding for a Tyrosine Ammonia Lyase (TAL), and/or a heterologous gene coding for a Phenylalanine Ammonia-Lyase (PAL) and a heterologous gene coding for a Cinnamate 4-Hydroxylase (C4H); and A heterologous gene coding for a Cytochrome P450 reductase (CPR1).

Preferably according to the invention, the heterologous gene coding for an HCT is a gene originating from a prokaryotic or eukaryotic organism, preferably *Arabidopsis thaliana* (At5g48930, GenBank, SEQ ID NO. 7).

Preferably according to the invention, the heterologous gene coding for a C3H is a gene originating from a prokaryotic or eukaryotic organism, preferably *Arabidopsis thaliana* (At2g40890, GenBank, SEQ ID NO. 5).

Preferably according to the invention, the heterologous gene coding for a CPR1 is a gene originating from a prokaryotic or eukaryotic organism, preferably *Catharanthus roseus*(X69791.1, GenBank, SEQ ID NO. 6).

Preferably according to the invention, the heterologous gene coding for a TAL is a gene originating from a prokaryotic or eukaryotic organism, preferably *Rhodotorula glutinis* (KF765779.1, GenBank, SEQ ID NO. 14).

Preferably according to the invention, said method of modifying a microorganism, preferably a yeast, to produce caffeic acid further comprises the introduction of:

A gene coding for a 3-deoxy-7-phosphoheptulonate synthase (ARO4) mutated so that the product is resistant to feedback inhibition compared to the parent gene; and/or A gene coding for a chorismate mutase (ARO7) mutated so that the product is resistant to feedback inhibition compared to the parent gene.

Preferably according to the invention, said method of modifying a microorganism, preferably a yeast, to produce caffeic acid further comprises the invalidation for:

a gene coding for a Phenylpyruvate decarboxylase (ARO10).

According to one embodiment of the invention, said method of modifying a microorganism, preferably a yeast, to produce caffeic acid further comprises introducing:

A gene coding for a 3-deoxy-7-phosphoheptulonate synthase (ARO4) mutated so that the product is resistant to feedback inhibition compared to the parent gene; and/or A gene coding for a chorismate mutase (ARO7) mutated so that the product is resistant to feedback inhibition compared to the parent gene; and/or invalidation of:

a gene coding for a Phenylpyruvate decarboxylase (ARO10).

Preferably, the ARO4 gene is mutated so that the amino acid at position 229 is a Leucine (K229L).

Preferably, the ARO7 gene is mutated so that the amino acid at position 141 is a Serine (G141S).

Preferably according to the invention, said yeast is a species of the Ascomycota phylum, preferably chosen from the genera Schizosaccharomycetes, *Saccharomyces, Kluyveromyces, Komagataella, Scheffersomyces, Torulaspora* and/or *Zygosaccharomyces*.

Preferably according to the invention, said yeast is of the *Saccharomyces cerevisiae* species.

According to one embodiment, the invention relates to a method of modifying a microorganism, preferably a yeast, to produce ferulic acid.

Preferably, the invention relates to a process for modifying a microorganism, preferably a yeast, to produce ferulic acid from the caffeic acid obtained, further comprising introducing:

A heterologous gene coding for caffeoyl-Omethyl Transferase (COMT).

Preferably, said method of modifying a microorganism, preferably a yeast, to produce ferulic acid from the caffeic acid obtained, further comprises introducing:

A gene coding for S-Adenosylmethyltransferase (SAM2).

Preferably, the SAM2 gene is the SAM2 gene of *Saccharomyces cerevisiae* and is a copy of the one naturally comprised (YDR502C, SGD Database, SEQ ID NO. 11).

Preferably according to the invention, the heterologous gene coding for COMT is a gene originating from a prokaryotic or eukaryotic organism, preferably *Arabidopsis thaliana* (At5g54160, GenBank, SEQ ID NO. 2).

Preferably, said method of modifying a microorganism, preferably a yeast, to produce ferulic acid from the caffeic acid obtained according to the invention further comprises the invalidation of the gene coding for a ferulic acid decarboxylase 1 (FDC1).

According to a third aspect, the invention relates to a method for producing caffeic acid, comprising a step of:

a. Cultivating recombinant microorganisms, preferably recombinant yeasts, as defined according to the invention in a culture medium.

Preferably, said method for producing caffeic acid further comprises a step of:

b. Recovering the caffeic acid obtained in step a.

According to the invention, "recovery" means isolating the target compound, here caffeic acid and/or ferulic acid, from the rest of the other compounds.

Examples of methods for recovering caffeic acid and ferulic acid are described in the literature, in particular in Yin Y. et al., "Polydopamine-coated magnetic molecularly imprinted polymer for the selective solid-phase extraction of cinnamic acid, ferulic acid and caffeic acid from radix scrophulariae sample," J Sep Sci. 2016 April; 39(8):1480-8, and in Ning Li. et al., "Separation and purification of the antioxidant compounds, caffeic acid phenethyl ester and caffeic acid from mushrooms by molecularly imprinted polymer," Food Chem. 2013 Aug. 15; 139(1-4):1161-7.

Preferably according to the invention, the caffeic acid is produced from glucose, p-coumaric acid, p-coumaroyl-shikimate and/or caffeoyl-shikimate, added to the culture medium before or in step a.

Even more preferably, the caffeic acid is produced from glucose.

According to a fourth aspect, the invention relates to a method for producing ferulic acid, comprising a step of:

a. Cultivating recombinant microorganisms, preferably recombinant yeasts, as defined according to the invention in a culture medium.

Preferably, said method for producing ferulic acid further comprises a step of:

b. Recovering the ferulic acid obtained in step a.

According to one embodiment, said method for producing caffeic acid and/or ferulic acid comprises a step of:

a. Cultivating recombinant microorganisms, preferably recombinant yeasts, capable of producing caffeic acid as defined according to the invention in a culture medium, or of a'. Cultivating recombinant microorganisms, preferably recombinant yeasts, capable of producing ferulic acid from the caffeic acid obtained according to the invention in a culture medium;

step a or a' preferably being followed by a step of:

b. Recovering the caffeic acid and/or the ferulic acid obtained in step a. or a'.

Preferably according to the invention, ferulic acid is produced from glucose, p-coumaric acid, p-coumaroyl-shikimate and/or caffeoyl-shikimate, added to the culture medium before or in step a or a'.

Preferably, the ferulic acid is produced from glucose.

According to a fifth aspect, the invention relates to a method for producing caffeic acid and/or ferulic acid, comprising a step of:

a. Cultivating recombinant microorganisms, preferably recombinant yeasts, capable of producing ferulic acid from the caffeic acid obtained as defined according to the invention in a culture medium.

Preferably, said method for producing caffeic acid and/or ferulic acid further comprises a step of:

b. Recovering the caffeic acid and/or the ferulic acid obtained in step a.

Preferably according to the invention, the caffeic acid and/or the ferulic acid are produced from glucose, p-coumaric acid, p-coumaroyl-shikimate and/or caffeoyl-shikimate, added in the culture medium before or in step a.

Preferably, the caffeic acid and/or the ferulic acid are produced from glucose.

According to a sixth aspect, the invention relates to the use of the recombinant microorganism, preferably the recombinant yeast, capable of producing ferulic acid from the caffeic acid obtained according to the invention to produce caffeic acid and/or ferulic acid.

According to a seventh aspect, the invention relates to the use of the recombinant microorganism, preferably the recombinant yeast, producing caffeic acid according to the invention to produce caffeic acid.

According to an eighth aspect, the invention relates to the use of the recombinant microorganism, preferably the recombinant yeast, producing ferulic acid according to the invention to produce ferulic acid.

Preferably, the ferulic acid is produced from caffeic acid produced by said recombinant microorganism, preferably said recombinant yeast, according to the invention.

According to a ninth aspect, the invention relates to at least one expression vector for the production of caffeic acid in a recombinant host microorganism, preferably a recombinant host yeast, comprising a sequence coding for a gene heterologous to the microorganism recombinant host, preferably recombinant host yeast, coding an enzyme of the hydrolase family capable of breaking, preferably hydrolyzing, the caffeoyl-shikimate bond to produce caffeic acid from caffeoyl-shikimate.

Preferably, the enzyme capable of breaking, preferably hydrolyzing, the caffeoyl-shikimate bond to produce caffeic acid from caffeoyl-shikimate is a caffeoyl-shikimate esterase (CSE).

Preferably according to the invention, the heterologous gene coding for a CSE is a gene originating from a prokaryotic or eukaryotic organism.

According to one embodiment, the heterologous gene coding for a CSE is the *Medicago truncatula* CSE (MtCSE) gene (XM_003609990.3, Genbank, SEQ ID NO. 9) or a gene coding for a sequence having at least 55, 60, 70, 80, 85, 90 or 95% identity with the amino acid sequence of *Medicago truncatula* CSE (MtCSE) and exhibiting caffeoyl-shikimate esterase activity.

According to one embodiment, the heterologous gene coding for a CSE is the *Arabidopsis thaliana* CSE (AtCSE) gene (At1g52760, GenBank, SEQ ID NO. 3) or a gene coding for a sequence having at least 55, 60, 70, 80, 85, 90 or 95% identity with the amino acid sequence of *Arabidopsis thaliana* CSE (AtCSE) and exhibiting caffeoyl-shikimate esterase activity.

According to one embodiment, the enzyme capable of breaking, preferably hydrolyzing, the caffeoyl-shikimate bond to produce caffeic acid from caffeoyl-shikimate is a chlorogenic acid esterase (ChlE).

According to one embodiment, the heterologous gene for a ChlE is the ChlE gene of *Bifidobacterium animalis* subsp. *Lactis* (BiChlE) (CP001606.1:789353-790141, GenBank, SEQ ID NO. 4) or a gene coding for a sequence having at least 55, 60, 70, 80, 85, 90 or 95% identity with the amino acid sequence of ChlE from *Bifidobacterium animalis* subsp. *Lactis* (BiChlE) and exhibiting chlorogenic acid esterase activity.

According to one embodiment, the heterologous gene for a ChlE is the ChlE gene from *Ustilago maydis* (UmChlE) (HG970190.1, GenBank, SEQ ID NO. 15) or a gene coding for a sequence having at least 55, 60, 70, 80, 85, 90 or 95% identity with the amino acid sequence of *Ustilago maydis* ChlE (UmChlE) and exhibiting chlorogenic acid esterase activity.

According to one embodiment, the heterologous gene for a ChlE is the ChlE gene of *Lactobacillus johnsonii* (LaChlE) (SPP101000004.1:37780-38526, GenBank, SEQ ID NO. 8) or a gene coding for a sequence having at least 55, 60, 70, 80, 85, 90 or 95% identity with the amino acid sequence of *Lactobacillus johnsonii* ChlE (LaChlE) and exhibiting chlorogenic acid esterase activity.

According to one embodiment, the heterologous gene for ChlE is the *Salinibacter ruber* ChlE (SrChlE) gene (CP030369.1:2322200-2323400, GenBank, SEQ ID NO. 13) or a gene coding for a sequence having at least 55, 60, 70, 80, 85, 90 or 95% identity with the amino acid sequence of *Salinibacter ruber* ChlE (SrChlE) and exhibiting chlorogenic acid esterase activity.

Preferably according to the invention, said at least one expression vector for the production of caffeic acid in a recombinant host microorganism, preferably a recombinant host yeast, further comprises a sequence coding for a heterologous gene coding for an enzyme capable of catalyzing the formation of the bond between coumaric acid and coenzyme A.

Preferably, the enzyme capable of catalyzing the formation of the bond between coumaric acid and coenzyme A is a 4-coumarate-CoA ligase (4CL).

Preferably according to the invention, the heterologous gene coding for a 4CL is a gene originating from a prokaryotic or eukaryotic organism.

Preferably according to the invention, the heterologous gene coding for a 4CL is mutated in order to reduce the affinity of said mutated 4CL for caffeic acid and to increase its specificity for p-coumaric acid compared to the parent gene. coding for an unmutated 4CL.

According to one embodiment, the 4CL is *Populus tomentosa* 4CL (AY043495, Genbank, SEQ ID NO. 10).

According to one embodiment, in the case where the 4CL is 4CL from *Populus tomentosa*, the amino acid:

- at position 236 is an Alanine (Y236A) or a Phenylalanine (Y236F); and/or
- at position 240 is an Alanine (S240A); and/or
- at position 305 is an Alanine (G305A); and/or
- at position 329 is an Alanine (G329A) According to one embodiment, the 4CL is *Arabidopsis thaliana* 4CL (At1g51680, GenBank, SEQ ID NO. 1).

According to one embodiment, in the case where the 4CL is the 4CL of *Arabidopsis thaliana*, the amino acid:

- at position 264 is an Alanine (S264A); and/or
- at position 329 is an Alanine (G329A); and/or
- at position 353 is an Alanine (G353A).

According to one embodiment, the 4CL is *Streptomyces coelicolor* 4CL (CAB95894.1, Genbank, SEQ ID NO. 12).

Preferably according to the invention, said at least one expression vector for the production of caffeic acid in a recombinant host microorganism, preferably a recombinant host yeast, further comprises a coding sequence for:

- A heterologous gene coding for a Hydroxycinnamoyl-Transferase (HCT); and
- A heterologous gene coding for a Coumarate 3 Hydroxylase (C3H); and
- A heterologous gene coding for a Tyrosine Ammonia Lyase (TAL), and/or a heterologous gene coding for a Phenylalanine Ammonia-Lyase (PAL) and a heterologous gene coding for a Cinnamate 4-Hydroxylase (C4H).

Preferably according to the invention, said at least one expression vector for the production of caffeic acid in a recombinant host microorganism, preferably a recombinant host yeast, further comprises a sequence coding for:

- A heterologous gene coding for a Cytochrome P450 reductase (CPR1).

According to one embodiment of the invention, said at least one expression vector for the production of caffeic acid in a recombinant host microorganism, preferably a recombinant host yeast, further comprises a sequence coding for:

- A heterologous gene coding for a Hydroxycinnamoyl-Transferase (HCT); and
- A heterologous gene coding for a Coumarate 3 Hydroxylase (C3H); and
- A heterologous gene coding for a Tyrosine Ammonia Lyase (TAL), and/or a heterologous gene coding for a Phenylalanine Ammonia-Lyase (PAL) and a heterologous gene coding for a Cinnamate 4-Hydroxylase (C4H); and
- A heterologous gene coding for a Cytochrome P450 reductase (CPR1).

Preferably according to the invention, the heterologous gene coding for an HCT is a gene originating from a prokaryotic or eukaryotic organism, preferably *Arabidopsis thaliana* (At5g48930, GenBank, SEQ ID NO. 7).

Preferably according to the invention, the heterologous gene coding for a C3H is a gene originating from a prokaryotic or eukaryotic organism, preferably *Arabidopsis thaliana* (At2g40890, GenBank, SEQ ID NO. 5).

Preferably according to the invention, the heterologous gene coding for a CPR1 is a gene originating from a prokaryotic or eukaryotic organism, preferably *Catharanthus roseus*(X69791.1, GenBank, SEQ ID NO. 6).

Preferably according to the invention, the heterologous gene coding for a TAL is a gene originating from a prokaryotic or eukaryotic organism, preferably *Rhodotorula glutinis* (KF765779.1, GenBank, SEQ ID NO. 14).

Preferably according to the invention, said at least one expression vector for the production of caffeic acid in a recombinant host microorganism, preferably a recombinant host yeast, further comprises a sequence coding for:

- A gene coding for a 3-deoxy-7-phosphoheptulonate synthase (ARO4) mutated so that the product is resistant to feedback inhibition compared to the parent gene; and/or
- A gene coding for a chorismate mutase (ARO7) mutated so that the product is resistant to feedback inhibition compared to the parent gene.

Preferably according to the invention, said at least one expression vector for the production of caffeic acid in a recombinant host microorganism, preferably a recombinant host yeast, further comprises a sequence allowing the invalidation of:

- a gene coding for Phenylpyruvate decarboxylase (ARO10).

According to one embodiment of the invention, said at least one expression vector for the production of caffeic acid in a recombinant host microorganism, preferably a recombinant host yeast, further comprises a sequence coding for:

- A gene coding for a 3-deoxy-7-phosphoheptulonate synthase (ARO4) mutated so that the product is resistant to feedback inhibition compared to the parent gene; and/or
- A gene encoding a chorismate mutase (ARO7) mutated so that the product is resistant to feedback inhibition compared to the parent gene; and/or invalidation of:
- a gene coding for a Phenylpyruvate decarboxylase (ARO10).

Preferably, the ARO4 gene is mutated so that the amino acid at position 229 is a Leucine (K229L).

Preferably, the ARO7 gene is mutated so that the amino acid at position 141 is a Serine (G141S).

According to one embodiment, said at least one expression vector in a recombinant host microorganism, preferably a recombinant host yeast, allows the production of ferulic acid from the caffeic acid obtained, and further comprises a sequence coding for:

- A heterologous gene coding for caffeoyl-Omethyl Transferase (COMT).

Preferably, said at least one expression vector in a recombinant host microorganism, preferably a recombinant host yeast, allowing the production of ferulic acid from the caffeic acid obtained further comprises a sequence coding for:

- A gene coding for S-Adenosylmethyltransferase (SAM2).

Preferably, said yeast is a species of the Ascomycota phylum, preferably chosen from the genera Schizosaccharomycetes, *Saccharomyces, Kluyveromyces, Komagataella, Scheffersomyces, Torulaspora* and/or *Zygosaccharomyces.*

Preferably, said yeast is of the *Saccharomyces Cerevisiae* species.

Preferably, the SAM2 gene is the *Saccharomyces cerevisiae* SAM2 gene and is a copy of the one naturally comprised (YDR502C, SGD Database, SEQ ID NO. 11).

Preferably according to the invention, the heterologous gene coding for COMT is a gene originating from a prokaryotic or eukaryotic organism, preferably *Arabidopsis thaliana* (At5g54160, UniProtKB).

Preferably, said at least one expression vector in a recombinant host microorganism, preferably a recombinant host yeast, allowing the production of ferulic acid from the caffeic acid obtained further comprises a sequence allowing the invalidation of the gene encoding a ferulic acid decarboxylase 1 (FDC1).

The invention can be better understood on reading the detailed description that follows of non-limiting example embodiments of the invention, and on examining the appended figures, in which:

DESCRIPTION OF THE FIGURES

FIG. 1 illustrates the hydrolysis reaction of caffeoyl-shikimate to caffeic acid and shikimate using caffeoyl-shikimate esterase (CSE) according to the invention.

FIG. 2 illustrates the metabolic pathways for the production of caffeic acid and ferulic acid in yeast according to one embodiment of the invention.

EXAMPLES

Example 1: Materials and Methods

Figure 3:
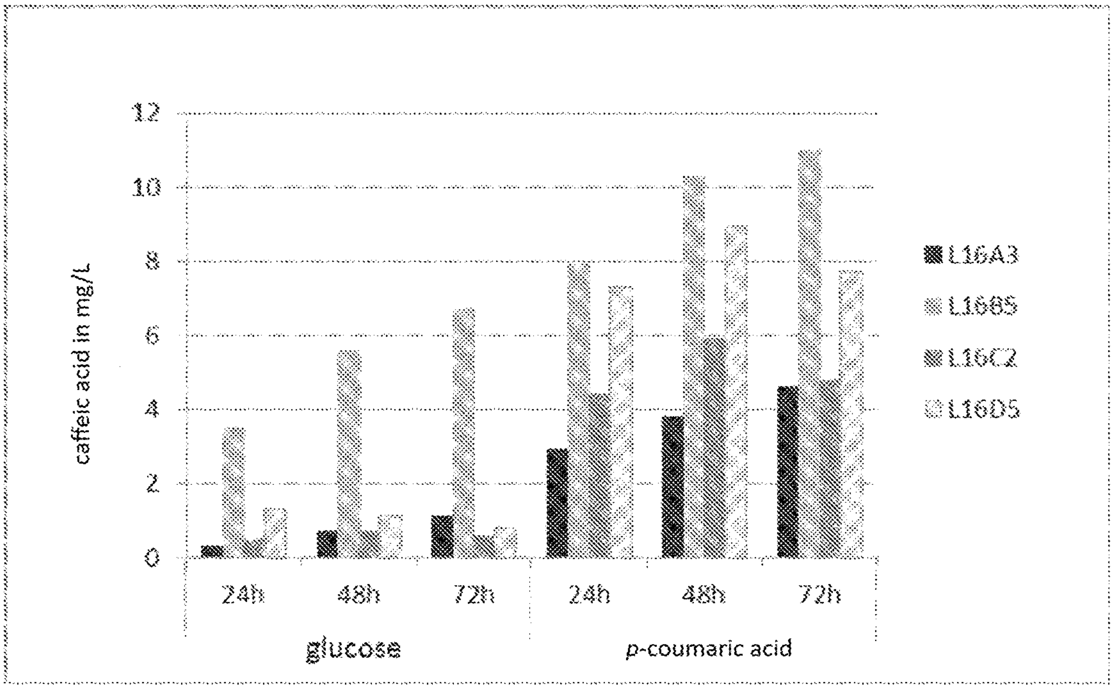
FIG. 3 illustrates the production of caffeic acid in a recombinant yeast according to one embodiment of the invention from p-coumaric or glucose via a CSE (UHPLC-TQ method), at 24 h, 48 h and 72 h.

The standards for p-coumaric acid, caffeic acid and ferulic acid were obtained from the supplier Sigma-Aldrich.

Gene Cloning:

The ARO4 (NP_009808, Genbank) and ARO7 (NP_015385, Genbank) genes were amplified by PCR from *S. cerevisiae* genomic DNA and then mutated so that their product was resistant to feedback inhibition (FBR: Feed Back Resistance) (Gold et al. Microbial Cell Factories (2015)). 14:73, see pages 11 to 16 and additional files). For ARO4, this corresponds to the K229L mutation, and for ARO7 to the G141S mutation.

The genes obtained by synthesis or PCR comprise, at the 5' and 3' end, a Bbs I (GAAGAC) or Bsa I (GGTCTC) restriction site, compatible with the cloning system used. All genes, promoters and terminators were restriction cloned into the pSBK vector. Promoters and terminators (Wargner et al., 2015) were amplified by PCR from the genomic DNA of the yeast *S. cerevisiae.*

The pSBK vector includes a yeast selection marker: URA3, LEU2 or TRP1.

TABLE 1

The various genes used to produce a recombinant yeast according to the invention.

| Gene | Accession number, bank | Origin |
|---|---|---|
| TAL (Tyrosine Ammonia Lyase) | KF765779.1, GenBank, SEQ ID NO. 14 | *Rhodotorula glutinis* |
| 4CL (4 Coumarate-CoA Ligase) | AY043495, Genbank, SEQ ID NO. 10 | *Populus tomentosa* |
| HCT (Hydroxycinnamoyl-Transferase) | At5g48930, GenBank, SEQ ID NO. 7 | *Arabidopsis thaliana* |
| C3H (Coumarate 3 Hydroxylase) | At2g40890, GenBank, SEQ ID NO. 5 | *Arabidopsis thaliana* |
| MtCSE (Caffeoyl-Shikimate Esterase) | XM_003609990.3, Genbank, SEQ ID NO. 9 | *Medicago truncatula* |
| AtCSE | At1g52760, GenBank, SEQ ID NO. 3 | *Arabidopsis thaliana* |
| COMT (Caffeoyl-O-Methyl Transferase) | At5g54160, GenBank, SEQ ID NO. 2 | *Arabidopsis thaliana* |
| CPR1 (Cytochrome P450 reductase) | X69791.1, GenBank, SEQ ID NO. 6 | *Catharanthus roseus* |
| SAM2 (S-Adenosylmethyltransferase) | YDR502C, SGD Database, SEQ ID NO. 11 | *Saccharomyces cerevisiae* |

Mutation of 4CL: *P. tomentosa* 4CL mutants Y236A and Y236F were constructed by PCR.

Deletion of Genes:

The ARO10 (YDR380W) and FDC1 (YDR539W) genes were invalidated by deletion, i.e. by integration instead of the open reading frame, of a linear DNA comprising a selection marker bounded by the regions upstream and downstream of the gene.

Strains:

The yeast model used in this study is the FY1679-28A strain of *Saccharomyces cerevisiae* (Tettelin et al., 1995—table 1 page 85), auxotrophic for uracil, tryptophan and leucine. The constructions were produced in the strain of *Escherichia coli* MH1 before their transfer to the yeast.

TABLE 2

| List of strains used | | |
|---|---|---|
| Name | Constructions | Markers |
| L16B5 | ARO4$^{K229L}$-ARO7$^{G141S}$ -TAL | URA3 |
| | 4CL$^{Y236A}$-HCT-C3H | TRP1 |
| | MtCSE-CPR1 | LEU2 |
| L16D5 | ARO4$^{K229L}$- ARO7$^{G141S}$ -TAL | URA3 |
| | 4CL$^{Y236F}$-HCT-C3H | TRP1 |
| | MtCSE-CPR1 | LEU2 |
| L16A3 | ARO4$^{K229L}$ -ARO7$^{G141S}$ -TAL | URA3 |
| | 4CL$^{Y236A}$-HCT-C3H | TRP1 |
| | AtCSE-CPR1 | LEU2 |
| L16C2 | ARO4$^{K229L}$ -ARO7$^{G141S}$-TAL | URA3 |
| | 4CL$^{Y236F}$-HCT-C3H | TRP1 |
| | AtCSE-CPR1 | LEU2 |
| L93-2D3 | fdc1Δ::(ARO4$^{K229L}$ -ARO7$^{G141S}$ -TAL)~HPH | HPH (hygromycin) |

TABLE 2-continued

| List of strains used | | |
|---|---|---|
| Name | Constructions | Markers |
| | 4CL$^{Y236A}$-HCT-C3H | TRP1 |
| | MtCSE-COMT- CPR1-SAM2 | URA3 |

All strains listed in this table have been invalidated for the ARO10 gene.

Cultivation Conditions:

The yeast strains were cultured for 72 h at 30° C., in a 24-well plate, with continuous shaking (200 RPM), in 1 mL of SD medium (Dutscher, Brumath, Fr) supplemented or not with CSM (Complete Supplement Mixture; Formedium, UK). Glucose is added at 20 g/L or p-coumaric acid was added to the medium at a concentration of 100 mg·l-1.

Analytical method: UHPLC-TQ method:

Sample preparation: Samples of 100 μL are collected for each experiment. 50 μL is transferred to a new plate, to which 50 μL of the internal standard solution is added. Each sample is then homogenized by suction-discharge, then centrifuged for 5 min at 3000 rpm at room temperature. The final concentration of the internal standard (Protocatechuic Acid) is 0.5 mg/L.

Analysis by UHPLC-TQ: The samples were analyzed by a UHPLC Vanquish-H (Thermo) coupled to a triple-quadrupole UHPLC-TQ (Thermo). The column is a Waters Acquity UPLC® USST3 column (8 μm 2.1×100 mm) associated with an HSST3 1.8 μm 2.1×5 mm pre-column.

Mobile phase A is a solution of 0.1% formic acid in LC/MS-grade water and mobile phase B is a solution of 0.1% formic acid in pure acetonitrile of LC/MS quality. The column temperature is 50° C. and the autosampler temperature is 10° C.

TABLE 3

| Chromatographic conditions for the detection of molecules of interest: | | | |
|---|---|---|---|
| Time (min) | Flow (mL/min) | Mobile phase A (%) | Mobile phase B (%) |
| 0 | 0.5 | 90 | 10 |
| 3.5 | 0.5 | 72 | 28 |
| 5.5 | 0.5 | 72 | 28 |
| 5.7 | 0.5 | 90 | 10 |
| 6.8 | 0.5 | 90 | 10 |

The parameters of the electrospray source are:
positive mode spray voltage at 4000 V
curtain gas: at 50 Arb
auxiliary gas at 15 Arb
temperature of the transfer tube at 300° C.
vaporizer temperature at 300° C.

TABLE 4

| Ions monitored and fragmentation conditions for the molecules of interest: | | | | | | |
|---|---|---|---|---|---|---|
| Molecules | Retention time (min) | Polarity | Precursor ion | Daughter ion | Collision energy | RF lens (V) |
| P-Coumaric | 2.21 | Negative | 162.9 | 119.054 | 14.55 | 87 |
| Acid | | | | 93 | 31.15 | 87 |
| Trans-ferulic | 2.67 | Negative | 192.95 | 149.06 | 11.33 | 93 |
| Acid | | | | 178.018 | 12.46 | 93 |
| Caffeic | 2.69 | Negative | 178.9 | 135 | 15.31 | 91 |
| Acid | | | | 107.071 | 21.34 | 91 |

UHPLC-HRMS method (High Resolution Mass Spectrometry):

Sample preparation: Samples of 100 μL are collected for each experiment. 50 μL is transferred to a new plate, to which 50 μL of acetonitrile is added. Each sample is then homogenized by suction-discharge, then centrifuged for 5 min at 3000 rpm at room temperature.

Analysis by UHPLC-HRMS: The samples were analyzed by a UHPLC Vanquish-H (Thermo) coupled to a UHPLC-HRMS. The column is a Waters Acquity UPLC® USST3 column (8 μm 2.1×100 mm) associated with an HSST3 1.8 μm 2.1×5 mm pre-column.

Mobile phase A is a solution of 0.1% formic acid in LC/MS-grade water and mobile phase B is a solution of 0.1% formic acid in pure acetonitrile of LC/MS quality. The column temperature is 50° C. and the autosampler temperature is 10° C.

TABLE 5

| Chromatographic conditions for the detection of molecules of interest: | | | |
|---|---|---|---|
| Time (min) | Flow (mL/min) | Mobile phase A (%) | Mobile phase B (%) |
| 0 | 0.5 | 100 | 0 |
| 0.5 | 0.5 | 100 | 0 |
| 1 | 0.5 | 88 | 12 |
| 4.7 | 0.5 | 84 | 16 |
| 5.5 | 0.5 | 55 | 45 |
| 6.5 | 0.5 | 55 | 45 |
| 9 | 0.5 | 0 | 100 |
| 10 | 0.5 | 0 | 100 |
| 10.5 | 0.5 | 100 | 0 |
| 12 | 0.5 | 100 | 0 |

The parameters of the electrospray source are:
positive mode spray voltage at 3.10 kV
curtain gas at 50 Arb
auxiliary gas at 20 Arb
capillary temperature at 350° C.
auxiliary gas heating temperature at 500° C.
S-lens RF at 55 V
collision energy (NCE in ramp): 20, 40, 60

TABLE 6

Tracked ions and fragmentation conditions for molecules of interest:

| Molecules | Retention time (min) | Polarity | Precursor ion | Fragments |
|---|---|---|---|---|
| P-Coumaric Acid | 4.18 | Negative | 163.04007 | 119.0502<br>93.0346 |
| Coumaroyl Shikimate | 5.09 | Negative | 319.08233 | 163.04007<br>119.05024<br>93.03459 |
| Caffeic Acid | 3.05 | Negative | 179.03498 | 135.0452 |
| Caffeoyl Shikimate | 3.70 | Negative | 335.07724 | 135.0452<br>179.0351 |

Example 2: Production of Caffeic Acid from Glucose or p-Coumaric Acid

The production of caffeic acid from glucose or p-coumaric acid was tested in 4 strains, the differences of which relate to the choice of the mutated 4CLs (either Y236A or Y236F) and the CSEs used (*A. thaliana* or *M. truncatula*).

FIG. 3 describes the results of the production of caffeic acid from p-coumaric or glucose by passing through a CSE (UHPLC-TQ method) using the yeast according to the invention. In all the strains tested, the ARO4K229L-ARO7G141S-TAL-HCT-C3H-CPR1 genes were added and the ARO10 gene was invalidated by deletion. These strains therefore diverge only by the 4CL and CSE used (L16A3: 4CLY236A-AtCSE; L16B5:4CLY236A-MtCSE; L16C2: 4CLY236F-AtCSE; L16D5:4CLY236F-MtCSE).

The results presented in FIG. 3 show that the combination of these different enzymes allows the production of caffeic acid.

The best condition is obtained with the 4CL Y236A mutation and the CSE of *M. truncatula* (L16B5).

Example 3: Production of the Various Intermediaries

Figure 4:
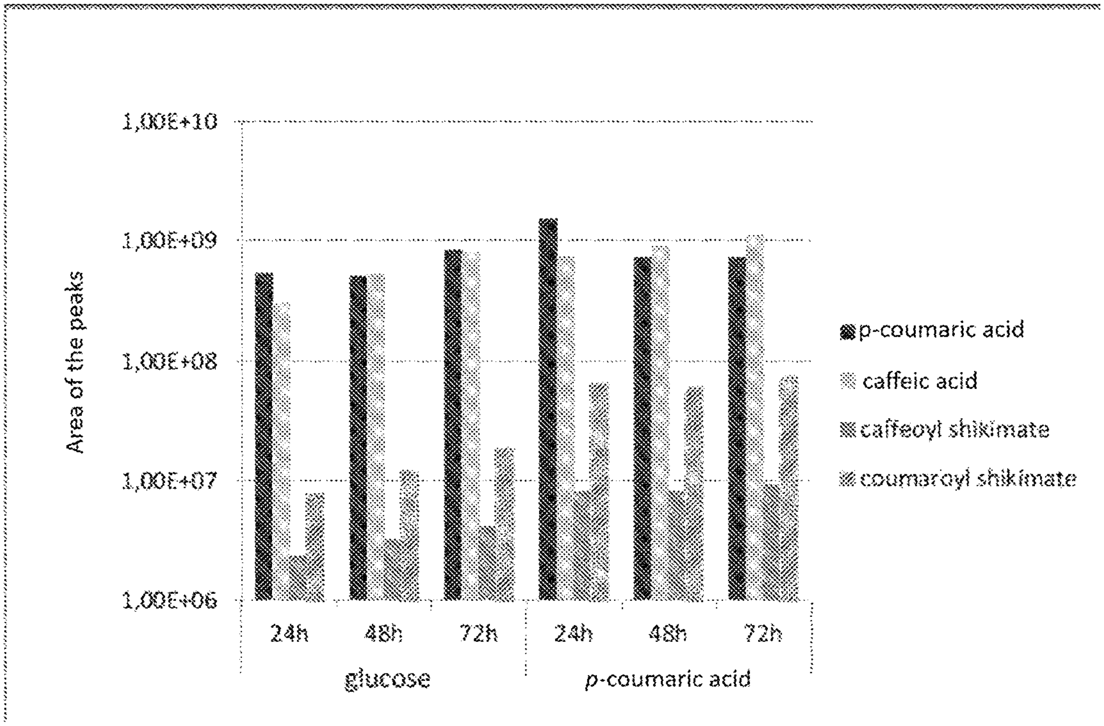
FIG. 4 illustrates the production of the various intermediates produced by the recombinant yeast according to one embodiment of the invention, analyzed by a qualitative method (UHPLC-HRMS method (high resolution mass spectrometry)).

The results presented in FIG. 4 show the characterization of the production of the various intermediates produced by the caffeic acid-producing yeast according to the invention from glucose or p-coumaric acid, by a qualitative method (UHPLC-HRMS method).

These results show the accumulation of each of the intermediates, i.e. p-coumaric acid, p-coumaroyl-shikimate, caffeoyl-shikimate and caffeic acid (see FIG. 4).

The accumulation of the various intermediates demonstrates the possibility of producing caffeic acid owing to the yeast according to the invention, as indicated by the presence of p-coumaroyl-shikimate and caffeoyl-shikimate.

Example 4: Production of Ferulic Acid from p-Coumaric Acid

The yeast according to the invention capable of producing ferulic acid possesses the methytransferase of *Arabidopsis thaliana* (COMT) and is invalidated for the FDC1 gene. This strain was incubated for 72 hours in the presence of p-coumaric acid and the production of caffeic acid and ferulic acid was determined by the UHPLC-TQ method.

Figure 5:
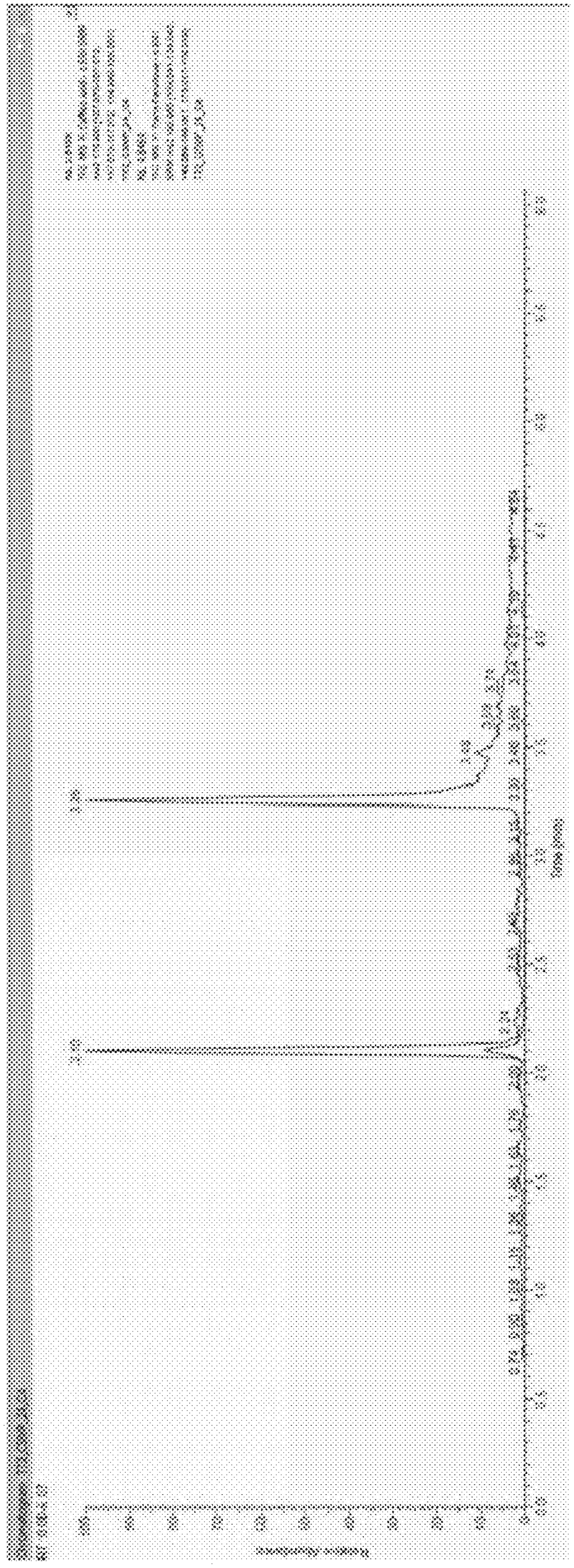
FIG. 5 illustrates the analysis of the compounds present in the recombinant yeast culture supernatant according to one embodiment of the invention, the presence of the compounds being determined by the UHPLC-TQ method. The first peak with a retention time of 2.1 min corresponds to caffeic acid and the second at 3.25 min to ferulic acid.

The chromatogram shows production of caffeic acid and ferulic acid (FIG. 5). The first peak with a retention time of 2.1 min corresponds to caffeic acid and the second at 3.25 min to ferulic acid.

These tests show that caffeic acid, produced from p-coumaric acid, can be efficiently converted into ferulic acid, when a methyl-transferase is added to the producing strain (FIG. 5).

Example 5: Production of Ferulic Acid from Glucose

The yeast according to the invention capable of producing ferulic acid possesses the methytransferase of *Arabidopsis thaliana* (COMT) and is invalidated for the FDC1 gene. This strain was incubated for 72 hours in the presence of glucose and the production of ferulic acid was determined by the UHPLC-TQ method.

Figure 6:
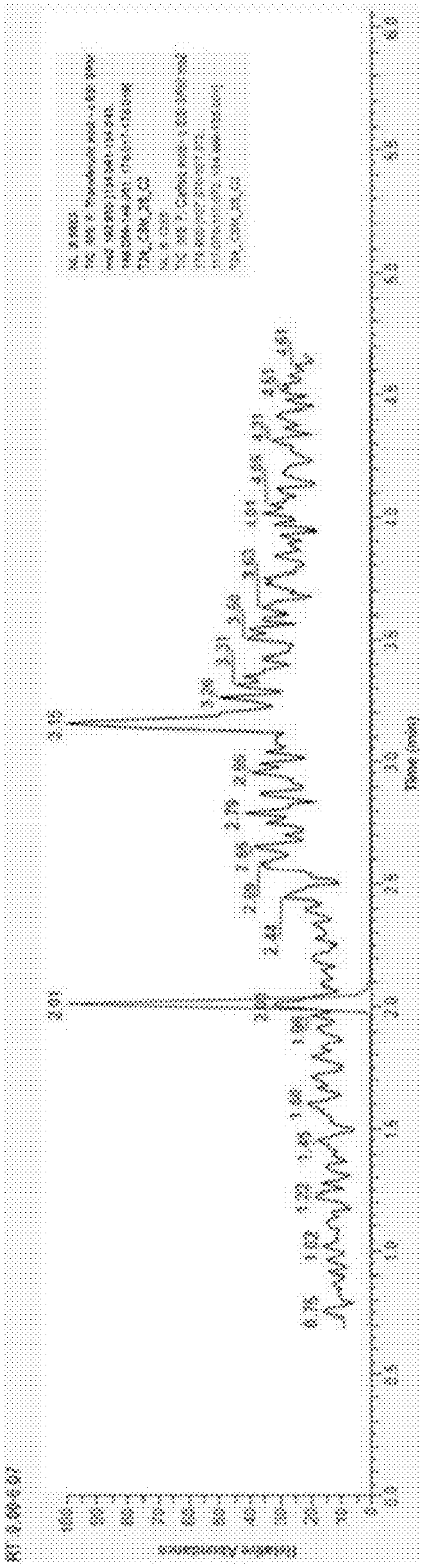
FIG. 6 is a chromatograph characterizing the production of ferulic acid in recombinant yeast according to one embodiment of the invention from glucose. The peak at 2.01 corresponds to caffeic acid and the peak at 3.15 corresponds to ferulic acid.

The chromatogram shows production of caffeic acid and ferulic acid (FIG. 6). The first peak with a retention time of 2.01 min corresponds to caffeic acid and the second at 3.15 min to ferulic acid.

These tests show that caffeic acid, produced from p-coumaric acid, can be efficiently converted into ferulic acid, when a methyl-transferase is added to the producing strain (FIG. 6).

Example 6: Test of the Hydrolysis of Caffeoyl-Shikimate into Caffeic Acid and Shikimate Using CSE The caffeoyl-shikimate sample was prepared from the culture supernatant of a producer strain. The release of caffeic acid from caffeoyl-shikimate was tested using a CSE-containing strain from *Medicago truncatula* (MtCSE).

Figure 7:
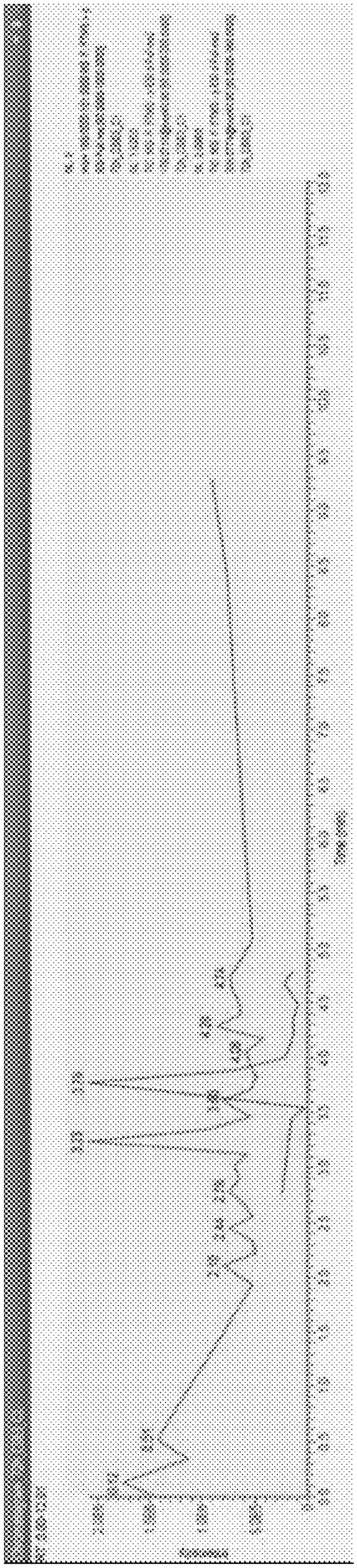
FIG. 7 is a chromatogram characterizing the hydrolysis of caffeoyl-shikimate into caffeic acid and shikimate using CSE (from *Medicago truncatula*, MtCSE) in recombinant yeast according to one embodiment of the invention. The peak with a retention time of 3.23 min corresponds to caffeic acid and the second at 3.78 min to caffeoyl-shikimate.

The results are shown in FIG. 7, the first peak with a retention time of 3.23 min corresponding to caffeic acid and the second at 3.78 min to caffeoyl-shikimate.

A production of caffeic acid from caffeoyl-shikimate in the presence of MtCSE is observed.

Example 7: Test of the Hydrolysis of Caffeoyl-Shikimate into Caffeic Acid and Shikimate Using ChLE The caffeoyl-shikimate sample was prepared from the culture supernatant of a producer strain. The release of caffeic acid from caffeoyl-shikimate was tested using a ChIE-containing strain of *Lactobacillus johnsonii*.

Figure 8:
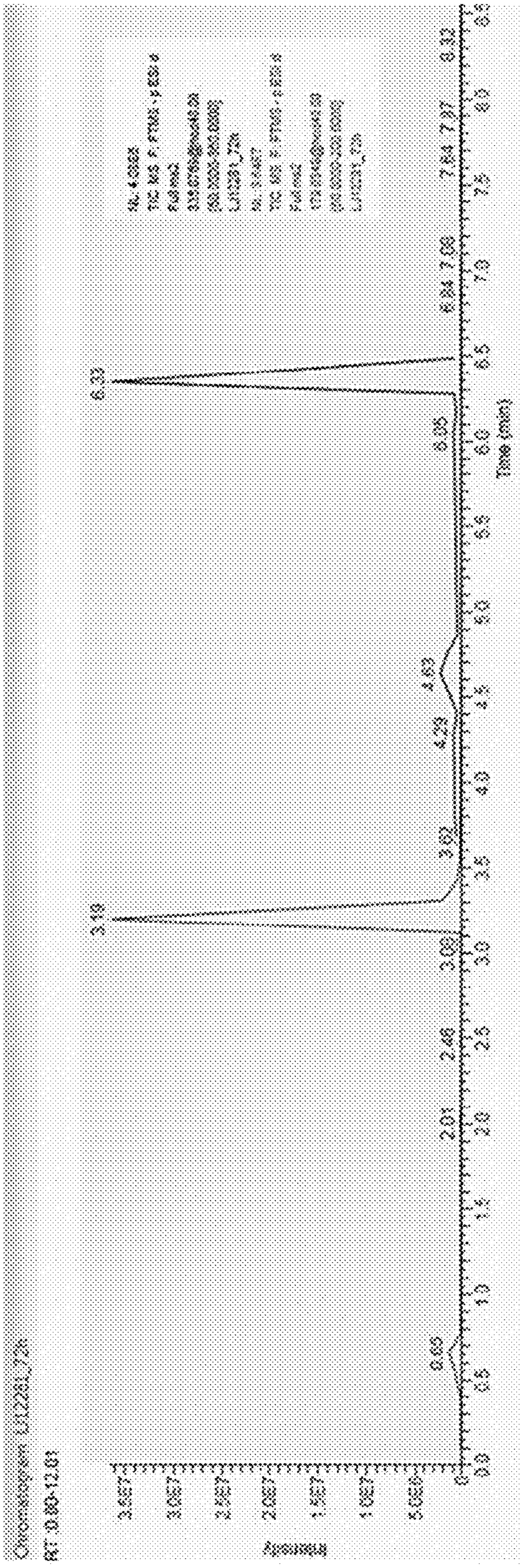
FIG. 8 is a chromatogram characterizing the hydrolysis of caffeoyl-shikimate into caffeic acid and shikimate owing to ChlE (from *Lactobacillus johnsonii*, LaChlE) in recombinant yeast according to one embodiment of the invention. The peak with a retention time of 3.19 min corresponds to caffeic acid.
Figure 9:
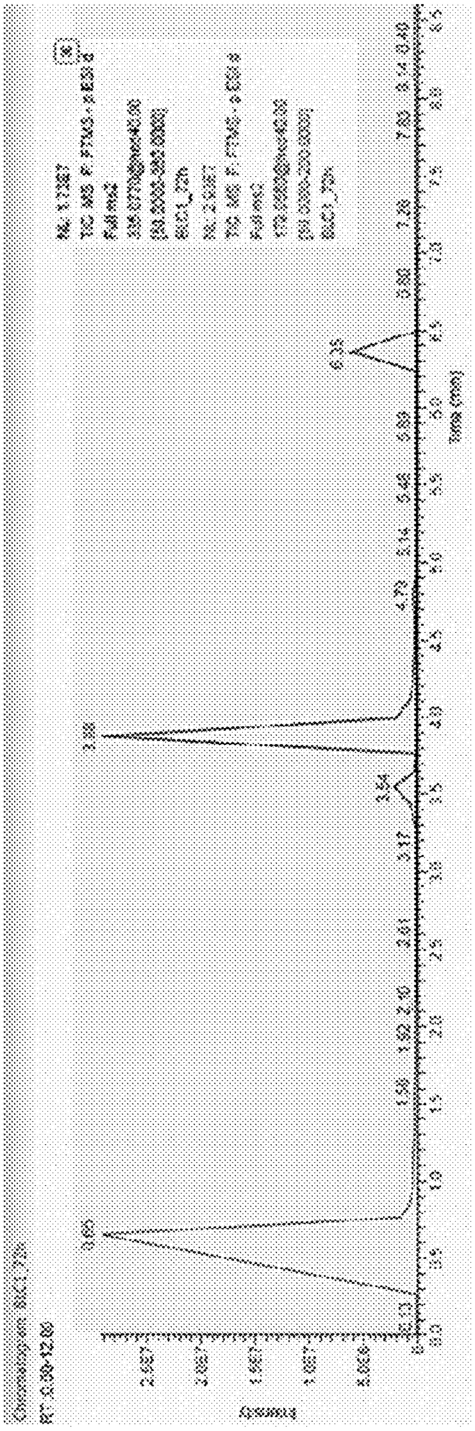
FIG. 9 is a chromatogram characterizing the presence of caffeoyl-shikimate in the control samples. The peak with a retention time of 3.88 min corresponds to caffeoyl-shikimate.

The results are shown in FIG. 8. A peak is observed at a retention time of 3.19 min corresponding to caffeic acid, all the caffeoyl-shikimate having been consumed. In FIG. 9 representing a control sample, it is possible to verify the presence of caffeoyl-shikimate, for which a peak is observed at 3.88 min, and the absence of caffeic acid.

A production of caffeic acid from caffeoyl-shikimate is observed in the presence of LaChIE.

The invention claimed is:

1. A recombinant yeast capable of producing caffeic acid, characterized in that it comprises:

a heterologous gene coding for an enzyme of the hydrolase family capable of hydrolyzing the caffeoyl-shikimate bond to produce caffeic acid from caffeoyl-shikimate, said enzyme being a caffeoyl-shikimate esterase (CSE) selected from a CSE of *Medicago truncatula* having an amino acid sequence corresponding to SEQ ID NO: 9, or a CSE of *Arabidopsis thaliana* having an amino acid sequence corresponding to SEQ ID NO: 3;

a heterologous gene coding for an enzyme capable of catalyzing the formation of the bond between coumaric acid and coenzyme A, said enzyme being a 4-coumarate-CoA ligase (4CL), said 4CL being selected from:

a 4CL gene of *Populus tomentosa* having an amino acid sequence corresponding to SEQ ID NO: 10, or a 4CL gene of *Arabidopsis thaliana* having an amino acid sequence corresponding to SEQ ID NO: 1, or a 4CL gene of *Streptomyces coelicolor* having an amino acid sequence corresponding to SEQ ID NO: 12; or a heterologous gene coding for a mutated 4CL having reduced affinity for caffeic acid and increased specificity for p-coumaric acid, wherein the mutations are:

in the case where the 4CL is the 4CL from *Populus tomentosa* having an amino acid sequence corresponding to SEQ ID NO: 10, the amino acid:

at position 236 is an Alanine (Y236A) or a Phenylalanine (Y236F); and/or at position 240 is an Alanine (S240A); and/or at position 305 is an Alanine (G305A); and/or at position 329 is an Alanine (G329A)

in the case where the 4CL is the 4CL of *Arabidopsis thaliana* having an amino acid sequence corresponding to SEQ ID NO: 1, the amino acid:

at position 264 is an Alanine (S264A); and/or at position 329 is an Alanine (G329A); and/or at position 353 is an Alanine (G353A).

2. The recombinant yeast according to claim 1, characterized in that said yeast is a species of the Ascomycota phylum.

3. The recombinant yeast according to claim 1, characterized in that said yeast is chosen from the genera *Schizosaccharomyces, Saccharomyces, Kluyveromyces, Komagataella, Scheffersomyces, Torulaspora* and/or *Zygosaccharomyces*.

4. The recombinant yeast according to claim 1, characterized in that said yeast is from the species *Saccharomyces cerevisiae*.

* * * * *